(12) United States Patent
Stone et al.

(10) Patent No.: US 8,298,262 B2
(45) Date of Patent: *Oct. 30, 2012

(54) METHOD FOR TISSUE FIXATION

(75) Inventors: Kevin T. Stone, Winona Lake, IN (US);
Gregory J. Denham, Warsaw, IN (US);
Ryan Harper, Leesburg, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 470 days.

This patent is subject to a terminal disclaimer.

(21) Appl. No.: 12/489,181

(22) Filed: Jun. 22, 2009

(65) Prior Publication Data

US 2009/0306711 A1  Dec. 10, 2009

Related U.S. Application Data

(63) Continuation-in-part of application No. 12/474,802, filed on May 29, 2009, now Pat. No. 8,088,130, and a continuation-in-part of application No. 11/541,506, filed on Sep. 29, 2006, now Pat. No. 7,601,165, and a continuation-in-part of application No. 11/541,505, filed on Sep. 29, 2006, now Pat. No. 7,658,751, and a continuation-in-part of application No. 12/014,399, filed on Jan. 15, 2008, now Pat. No. 7,909,851, and a continuation-in-part of application No. 12/014,340, filed on Jan. 15, 2008, now Pat. No. 7,905,904, and a continuation-in-part of application No. 11/935,681, filed on Nov. 6, 2007, now Pat. No. 7,905,903, and a continuation-in-part of application No. 11/869,440, filed on Oct. 9, 2007, now Pat. No. 7,857,830, and a continuation-in-part of application No. 11/784,821, filed on Apr. 10, 2007, and a continuation-in-part of application No. 11/347,661, filed on Feb. 3, 2006, now Pat. No. 7,749,250, and a continuation-in-part of application No. 11/347,662, filed on Feb. 3, 2006, now abandoned, and a continuation-in-part of application No. 12/196,405, filed on Aug. 22, 2008, now Pat. No. 8,128,658, and a continuation-in-part of application No. 12/196,407, filed on Aug. 22, 2008, now Pat. No. 8,137,382, and a continuation-in-part of application No. 12/196,410, filed on Aug. 22, 2008, now Pat. No. 8,118,836.

(51) Int. Cl.
*A61B 17/04* (2006.01)
*A61B 17/84* (2006.01)
*A61F 2/08* (2006.01)

(52) U.S. Cl. .................................. 606/232; 606/300

(58) Field of Classification Search .................. 606/300, 606/74, 103, 232, 223–228, 233, 60; 24/129 D, 24/115 H, 122.3, 131 C, 115 A; 289/2, 17
See application file for complete search history.

(56) References Cited

U.S. PATENT DOCUMENTS 65,499 A  6/1867  Miller
(Continued)

FOREIGN PATENT DOCUMENTS

AU  4957264  3/1966
(Continued)

OTHER PUBLICATIONS

"Do your next distal tendon repair with . . . The Lubbers Technique", Teno Fix® brochure, 2003 (2 pages) Ortheon® Medical.

(Continued)

*Primary Examiner* — Dianne Dornbusch
(74) *Attorney, Agent, or Firm* — Harness, Dickey

(57) ABSTRACT

A method for securing a strand to a fixation member for arthroscopic fixation, wherein the fixation member includes a channel on an exterior surface and an aperture therethrough. The method includes passing a strand having first and second ends through a flexible sleeve, passing the sleeve through the aperture of the fixation member in a first direction, tensioning the strand, and pulling the sleeve in a second direction different than the first direction to secure the sleeve to the fixation member without tying the strand on the fixation member.

13 Claims, 20 Drawing Sheets

U.S. PATENT DOCUMENTS

| | | | |
|---|---|---|---|
| 126,366 A | 4/1872 | Wills |
| 233,475 A | 10/1880 | Cook et al. |
| 261,501 A | 7/1882 | Vandermark |
| 268,407 A | 12/1882 | Hughes |
| 417,805 A | 12/1889 | Beaman |
| 487,304 A | 12/1892 | Todd |
| 762,710 A | 6/1901 | Hall |
| 837,767 A | 12/1906 | Aims |
| 838,203 A | 12/1906 | Aims |
| 1,059,631 A | 4/1913 | Popovics |
| 1,131,155 A | 9/1915 | Murphy |
| 1,153,450 A | 9/1915 | Schaff |
| 1,346,940 A | 7/1920 | Collins |
| 1,635,066 A | 7/1927 | Wells |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicka |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| RE22,857 E | 3/1947 | Ogburn |
| 2,526,959 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,988 A | 1/1955 | Brown |
| 2,760,488 A | 8/1956 | Pierce |
| 2,833,264 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| RE26,501 E | 12/1968 | Kendrick et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,810,456 A | 5/1974 | Karman |
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,446 A | 3/1976 | Schofield |
| 3,946,728 A | 3/1976 | Bettex et al. |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,036,101 A | 7/1977 | Burnett |
| 4,050,100 A | 9/1977 | Barry |
| 4,054,954 A | 10/1977 | Nakayama et al. |
| 4,085,466 A | 4/1978 | Goodfellow et al. |
| 4,094,313 A | 6/1978 | Komamura et al. |
| 4,099,750 A | 7/1978 | McGrew |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,149,277 A | 4/1979 | Bokros |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |

| | | |
|---|---|---|
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,307,723 A | 12/1981 | Finney |
| 4,312,337 A | 1/1982 | Donohue |
| 4,316,469 A | 2/1982 | Kapitanov et al. |
| 4,326,531 A | 4/1982 | Shimonaka et al. |
| 4,345,601 A | 8/1982 | Fukuda |
| 4,349,027 A | 9/1982 | DiFrancesco |
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,489,446 A | 12/1984 | Reed |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'Holla |
| 4,534,350 A | 8/1985 | Golden et al. |
| 4,535,764 A | 8/1985 | Ebert |
| 4,537,185 A | 8/1985 | Stednitz |
| 4,549,545 A | 10/1985 | Levy |
| 4,549,652 A | 10/1985 | Free |
| 4,561,432 A | 12/1985 | Mazor |
| 4,564,007 A | 1/1986 | Coombs et al. |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,590,928 A | 5/1986 | Hunt et al. |
| 4,595,007 A | 6/1986 | Mericle |
| 4,596,249 A | 6/1986 | Freda et al. |
| 4,602,635 A | 7/1986 | Mulhollan et al. |
| 4,602,636 A | 7/1986 | Noiles |
| 4,604,997 A | 8/1986 | De Bastiani et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |
| 4,636,121 A | 1/1987 | Miller |
| 4,641,652 A | 2/1987 | Hutterer et al. |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,777 A | 4/1987 | Dunn et al. |
| 4,662,068 A | 5/1987 | Polonsky |
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |
| 4,696,300 A | 9/1987 | Anderson |
| 4,705,040 A | 11/1987 | Mueller et al. |
| 4,708,132 A | 11/1987 | Silvestrini |
| 4,714,475 A | 12/1987 | Grundei et al. |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson et al. |
| 4,738,255 A | 4/1988 | Goble et al. |
| 4,741,330 A | 5/1988 | Hayhurst |
| 4,741,336 A | 5/1988 | Failla et al. |
| 4,744,353 A | 5/1988 | McFarland |
| 4,744,793 A | 5/1988 | Parr et al. |
| 4,750,492 A | 6/1988 | Jacobs |
| 4,760,843 A | 8/1988 | Fischer et al. |
| 4,760,844 A | 8/1988 | Kyle |
| 4,760,848 A | 8/1988 | Hasson |
| 4,770,663 A | 9/1988 | Hanslik et al. |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee et al. |
| 4,784,126 A | 11/1988 | Hourahane et al. |
| 4,787,882 A | 11/1988 | Claren et al. |
| 4,790,297 A | 12/1988 | Luque et al. |
| 4,793,363 A | 12/1988 | Ausherman et al. |
| 4,809,695 A | 3/1989 | Gwathmey et al. |
| 4,813,406 A | 3/1989 | Ogle, II |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,838,282 A | 6/1989 | Strasser et al. |
| 4,841,960 A | 6/1989 | Garner |
| 4,851,005 A | 7/1989 | Hunt et al. |
| 4,858,608 A | 8/1989 | McQuilkin et al. |
| 4,860,513 A | 8/1989 | Whitman |
| 4,863,383 A | 9/1989 | Grafelmann et al. |
| 4,870,957 A | 10/1989 | Goble et al. |
| 4,873,976 A | 10/1989 | Schreiber |
| 4,887,601 A | 12/1989 | Richards |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,923,461 A | 5/1990 | Caspari et al. |
| 4,927,421 A | 5/1990 | Goble et al. |
| 4,946,377 A | 8/1990 | Kovach |
| 4,946,468 A | 8/1990 | Li |
| 4,950,270 A | 8/1990 | Bowman et al. |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Tormala et al. |
| 4,969,886 A | 11/1990 | Cziffer et al. |
| 4,976,736 A | 12/1990 | White et al. |
| 4,978,350 A | 12/1990 | Wagenknecht et al. |
| 4,979,956 A | 12/1990 | Silvestrini |
| 4,983,176 A | 1/1991 | Cushman et al. |
| 4,988,351 A | 1/1991 | Paulos et al. |
| 4,994,074 A | 2/1991 | Bezwada et al. |
| 4,997,433 A | 3/1991 | Goble et al. |
| 5,002,550 A | 3/1991 | Li |
| 5,002,562 A | 3/1991 | Oberlander |
| 5,007,921 A | 4/1991 | Brown |
| 5,030,224 A | 7/1991 | Wright et al. |
| 5,030,235 A | 7/1991 | Campbell, Jr. |
| 5,037,422 A | 8/1991 | Hayhurst et al. |
| 5,041,129 A | 8/1991 | Hayhurst et al. |
| 5,046,513 A | 9/1991 | Gatturna et al. |
| 5,047,030 A | 9/1991 | Draenert et al. |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |

| Patent No. | Date | Inventor |
|---|---|---|
| 5,062,843 A | 11/1991 | Mahony, III |
| 5,064,431 A | 11/1991 | Gilbertson et al. |
| 5,074,874 A | 12/1991 | Yoon et al. |
| 5,078,731 A | 1/1992 | Hayhurst |
| 5,078,843 A | 1/1992 | Pratt |
| 5,084,050 A | 1/1992 | Draenert et al. |
| 5,084,058 A | 1/1992 | Li |
| 5,085,661 A | 2/1992 | Moss |
| 5,087,263 A | 2/1992 | Li |
| 5,089,012 A | 2/1992 | Prou |
| 5,092,866 A | 3/1992 | Breard et al. |
| 5,098,435 A | 3/1992 | Stednitz et al. |
| 5,100,415 A | 3/1992 | Hayhurst |
| 5,100,417 A | 3/1992 | Cerier et al. |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |
| 5,123,914 A | 6/1992 | Cope |
| 5,127,785 A | 7/1992 | Faucher et al. |
| 5,129,901 A | 7/1992 | Decoste |
| 5,129,902 A | 7/1992 | Goble et al. |
| 5,129,904 A | 7/1992 | Illi et al. |
| 5,129,906 A | 7/1992 | Ross et al. |
| 5,139,498 A | 8/1992 | Astudillo Ley |
| 5,139,499 A | 8/1992 | Small et al. |
| 5,139,520 A | 8/1992 | Rosenberg |
| 5,143,498 A | 9/1992 | Whitman |
| 5,147,362 A | 9/1992 | Goble |
| 5,149,329 A | 9/1992 | Richardson |
| 5,152,790 A | 10/1992 | Rosenberg et al. |
| 5,154,189 A | 10/1992 | Oberlander |
| 5,156,616 A | 10/1992 | Meadows et al. |
| 5,163,960 A | 11/1992 | Bonutti |
| D331,626 S | 12/1992 | Hayhurst et al. |
| 5,169,400 A | 12/1992 | Muhling et al. |
| 5,176,682 A | 1/1993 | Chow |
| 5,178,629 A | 1/1993 | Kammerer |
| 5,183,458 A | 2/1993 | Marx |
| 5,192,282 A | 3/1993 | Draenert et al. |
| 5,197,987 A | 3/1993 | Koch et al. |
| 5,203,784 A | 4/1993 | Ross et al. |
| 5,203,787 A | 4/1993 | Noblitt et al. |
| 5,207,679 A | 5/1993 | Li |
| 5,209,753 A | 5/1993 | Biedermann et al. |
| 5,209,805 A | 5/1993 | Spraggins |
| 5,211,647 A | 5/1993 | Schmieding |
| 5,211,650 A | 5/1993 | Noda |
| 5,214,987 A | 6/1993 | Fenton, Sr. |
| 5,219,359 A | 6/1993 | McQuilkin et al. |
| 5,222,976 A | 6/1993 | Yoon |
| 5,224,946 A | 7/1993 | Hayhurst et al. |
| 5,230,699 A | 7/1993 | Grasinger |
| 5,232,436 A | 8/1993 | Janevski |
| 5,234,435 A | 8/1993 | Seagrave, Jr. |
| 5,235,238 A | 8/1993 | Nomura et al. |
| 5,236,445 A | 8/1993 | Hayhurst et al. |
| 5,236,461 A | 8/1993 | Forte |
| 5,242,447 A | 9/1993 | Borzone |
| 5,246,441 A | 9/1993 | Ross et al. |
| 5,249,899 A | 10/1993 | Wilson |
| 5,250,053 A | 10/1993 | Snyder |
| 5,258,015 A | 11/1993 | Li et al. |
| 5,258,016 A | 11/1993 | DiPoto et al. |
| 5,258,040 A | 11/1993 | Bruchman et al. |
| 5,261,908 A | 11/1993 | Campbell, Jr. |
| 5,268,001 A | 12/1993 | Nicholson et al. |
| 5,269,160 A | 12/1993 | Wood |
| 5,269,783 A | 12/1993 | Sander |
| 5,269,806 A | 12/1993 | Sardelis et al. |
| 5,269,809 A | 12/1993 | Hayhurst et al. |
| 5,279,311 A | 1/1994 | Snyder |
| 5,281,422 A | 1/1994 | Badylak et al. |
| 5,282,809 A | 2/1994 | Kammerer et al. |
| 5,282,832 A | 2/1994 | Toso et al. |
| 5,282,867 A | 2/1994 | Mikhail |
| 5,285,040 A | 2/1994 | Brandberg et al. |
| 5,290,217 A | 3/1994 | Campos |
| 5,306,301 A | 4/1994 | Graf et al. |
| 5,312,422 A | 5/1994 | Trott |
| 5,312,438 A | 5/1994 | Johnson |
| 5,318,566 A | 6/1994 | Miller |
| 5,318,575 A | 6/1994 | Chesterfield et al. |
| 5,318,577 A | 6/1994 | Li |
| 5,318,578 A | 6/1994 | Hasson |
| 5,320,115 A | 6/1994 | Kenna |
| 5,320,626 A | 6/1994 | Schmieding |
| 5,320,633 A | 6/1994 | Allen et al. |
| 5,324,308 A | 6/1994 | Pierce |
| 5,330,489 A | 7/1994 | Green et al. |
| 5,333,625 A | 8/1994 | Klein |
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,339,870 A | 8/1994 | Green et al. |
| 5,342,369 A | 8/1994 | Harryman, II |
| 5,346,462 A | 9/1994 | Barber |
| 5,354,298 A | 10/1994 | Lee et al. |
| 5,356,412 A | 10/1994 | Golds et al. |
| 5,356,413 A | 10/1994 | Martins et al. |
| 5,356,417 A | 10/1994 | Golds |
| 5,358,511 A | 10/1994 | Gatturna et al. |
| 5,360,431 A | 11/1994 | Puno et al. |
| 5,362,294 A | 11/1994 | Seitzinger |
| 5,364,400 A | 11/1994 | Rego, Jr. et al. |
| 5,366,461 A | 11/1994 | Blasnik |
| 5,368,599 A | 11/1994 | Hirsch et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,379,492 A | 1/1995 | Glesser |
| 5,383,878 A | 1/1995 | Roger et al. |
| 5,383,904 A | 1/1995 | Totakura et al. |
| 5,391,171 A | 2/1995 | Schmieding |
| 5,391,176 A | 2/1995 | de la Torre |
| 5,391,182 A | 2/1995 | Chin |
| 5,393,302 A | 2/1995 | Clark et al. |
| RE34,871 E | 3/1995 | McGuire et al. |
| 5,397,356 A | 3/1995 | Goble et al. |
| 5,403,328 A | 4/1995 | Shallman |
| 5,403,329 A | 4/1995 | Hinchcliffe |
| 5,403,348 A | 4/1995 | Bonutti |
| 5,405,359 A | 4/1995 | Pierce |
| 5,417,691 A | 5/1995 | Hayhurst |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,860 A | 6/1995 | Lizardi et al. |
| 5,425,733 A | 6/1995 | Schmieding |
| 5,425,766 A | 6/1995 | Bowald et al. |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch et al. |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,722 A | 10/1995 | McLeod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |

| Patent | Kind | Date | Inventor |
|---|---|---|---|
| 5,464,427 | A | 11/1995 | Curtis et al. |
| 5,464,440 | A | 11/1995 | Johansson et al. |
| 5,466,237 | A | 11/1995 | Byrd, III et al. |
| 5,467,786 | A | 11/1995 | Allen et al. |
| 5,470,334 | A | 11/1995 | Ross et al. |
| 5,470,337 | A | 11/1995 | Moss |
| 5,470,338 | A | 11/1995 | Whitfield et al. |
| 5,472,452 | A | 12/1995 | Trott |
| 5,474,565 | A | 12/1995 | Trott |
| 5,474,568 | A | 12/1995 | Scott |
| 5,474,572 | A | 12/1995 | Hayhurst |
| 5,478,344 | A | 12/1995 | Stone et al. |
| 5,478,345 | A | 12/1995 | Stone et al. |
| 5,480,403 | A | 1/1996 | Lee et al. |
| 5,480,406 | A | 1/1996 | Nolan et al. |
| 5,484,442 | A | 1/1996 | Melker et al. |
| 5,486,197 | A | 1/1996 | Le et al. |
| 5,490,750 | A | 2/1996 | Gundy |
| 5,496,331 | A | 3/1996 | Xu et al. |
| 5,496,348 | A | 3/1996 | Bonutti |
| 5,500,000 | A | 3/1996 | Feagin et al. |
| 5,505,736 | A | 4/1996 | Reimels et al. |
| 5,507,754 | A | 4/1996 | Green et al. |
| 5,520,691 | A | 5/1996 | Branch |
| 5,520,700 | A | 5/1996 | Beyar et al. |
| 5,520,702 | A | 5/1996 | Sauer et al. |
| 5,522,817 | A | 6/1996 | Sander et al. |
| 5,522,820 | A | 6/1996 | Caspari et al. |
| 5,522,844 | A | 6/1996 | Johnson |
| 5,522,845 | A | 6/1996 | Wenstrom, Jr. |
| 5,522,846 | A | 6/1996 | Bonutti |
| 5,524,946 | A | 6/1996 | Thompson |
| 5,527,321 | A | 6/1996 | Hinchliffe |
| 5,527,342 | A | 6/1996 | Pietrzak et al. |
| 5,527,343 | A | 6/1996 | Bonutti |
| 5,534,012 | A | 7/1996 | Bonutti |
| 5,536,270 | A | 7/1996 | Songer et al. |
| 5,540,698 | A | 7/1996 | Preissman |
| 5,540,703 | A | 7/1996 | Barker, Jr. et al. |
| 5,540,718 | A | 7/1996 | Bartlett |
| 5,545,168 | A | 8/1996 | Burke |
| 5,545,178 | A | 8/1996 | Kensey et al. |
| 5,545,180 | A | 8/1996 | Le et al. |
| 5,545,228 | A | 8/1996 | Kambin |
| 5,549,613 | A | 8/1996 | Goble et al. |
| 5,549,617 | A | 8/1996 | Green et al. |
| 5,549,619 | A | 8/1996 | Peters et al. |
| 5,549,630 | A | 8/1996 | Bonutti |
| 5,549,631 | A | 8/1996 | Bonutti |
| 5,562,683 | A | 10/1996 | Chan |
| 5,562,685 | A | 10/1996 | Mollenauer et al. |
| 5,562,686 | A | 10/1996 | Sauer et al. |
| 5,569,269 | A | 10/1996 | Hart et al. |
| 5,569,305 | A | 10/1996 | Bonutti |
| 5,571,090 | A | 11/1996 | Sherts |
| 5,571,139 | A | 11/1996 | Jenkins, Jr. |
| 5,572,655 | A | 11/1996 | Tuljapurkar et al. |
| 5,573,286 | A | 11/1996 | Rogozinski |
| 5,573,542 | A | 11/1996 | Stevens |
| 5,573,548 | A | 11/1996 | Nazre et al. |
| 5,577,299 | A | 11/1996 | Thompson et al. |
| 5,578,057 | A | 11/1996 | Wenstrom, Jr. |
| 5,584,695 | A | 12/1996 | Lal Sachdeva et al. |
| 5,584,835 | A | 12/1996 | Greenfield |
| 5,584,836 | A | 12/1996 | Ballintyn et al. |
| 5,584,862 | A | 12/1996 | Bonutti |
| 5,586,986 | A | 12/1996 | Hinchliffe |
| 5,588,575 | A | 12/1996 | Davignon |
| 5,591,180 | A | 1/1997 | Hinchliffe |
| 5,591,181 | A | 1/1997 | Stone et al. |
| 5,591,207 | A | 1/1997 | Coleman |
| 5,593,407 | A | 1/1997 | Reis et al. |
| 5,593,425 | A | 1/1997 | Bonutti et al. |
| 5,601,557 | A | 2/1997 | Hayhurst |
| 5,601,559 | A | 2/1997 | Melker et al. |
| 5,601,571 | A | 2/1997 | Moss |
| 5,603,716 | A | 2/1997 | Morgan et al. |
| 5,607,429 | A | 3/1997 | Hayano et al. |
| 5,618,290 | A | 4/1997 | Toy et al. |
| 5,626,611 | A | 5/1997 | Liu et al. |
| 5,626,614 | A | 5/1997 | Hart |
| 5,628,756 | A | 5/1997 | Barker, Jr. et al. |
| 5,628,766 | A | 5/1997 | Johnson |
| 5,630,824 | A | 5/1997 | Hart |
| 5,632,748 | A | 5/1997 | Beck, Jr. et al. |
| 5,641,256 | A | 6/1997 | Gundy |
| 5,643,266 | A | 7/1997 | Li |
| 5,643,269 | A | 7/1997 | Harle et al. |
| 5,643,295 | A | 7/1997 | Yoon |
| 5,643,319 | A | 7/1997 | Green et al. |
| 5,643,320 | A | 7/1997 | Lower et al. |
| 5,643,321 | A | 7/1997 | McDevitt |
| 5,645,546 | A | 7/1997 | Fard |
| 5,645,547 | A | 7/1997 | Coleman |
| 5,645,568 | A | 7/1997 | Chervitz et al. |
| 5,645,588 | A | 7/1997 | Graf et al. |
| 5,647,874 | A | 7/1997 | Hayhurst |
| 5,649,959 | A | 7/1997 | Hannam et al. |
| 5,649,963 | A | 7/1997 | McDevitt |
| 5,658,289 | A | 8/1997 | Boucher et al. |
| 5,658,299 | A | 8/1997 | Hart |
| 5,658,313 | A | 8/1997 | Thal |
| 5,662,658 | A | 9/1997 | Wenstrom, Jr. |
| 5,662,663 | A | 9/1997 | Shallman |
| 5,665,112 | A | 9/1997 | Thal |
| 5,667,513 | A | 9/1997 | Torrie et al. |
| 5,671,695 | A | 9/1997 | Schroeder |
| 5,674,224 | A | 10/1997 | Howell et al. |
| 5,679,723 | A | 10/1997 | Cooper et al. |
| 5,681,334 | A | 10/1997 | Evans et al. |
| 5,681,352 | A | 10/1997 | Clancy, III et al. |
| 5,683,419 | A | 11/1997 | Thal |
| 5,688,285 | A | 11/1997 | Yamada et al. |
| 5,690,676 | A | 11/1997 | DiPoto et al. |
| 5,690,678 | A | 11/1997 | Johnson |
| 5,693,046 | A | 12/1997 | Songer et al. |
| 5,695,497 | A | 12/1997 | Stahelin et al. |
| 5,697,929 | A | 12/1997 | Mellinger |
| 5,699,657 | A | 12/1997 | Paulson |
| 5,702,397 | A | 12/1997 | Goble et al. |
| 5,702,422 | A | 12/1997 | Stone |
| 5,702,462 | A | 12/1997 | Oberlander |
| 5,707,373 | A | 1/1998 | Sevrain et al. |
| 5,711,969 | A | 1/1998 | Patel et al. |
| 5,713,005 | A | 1/1998 | Proebsting |
| 5,713,904 | A | 2/1998 | Errico et al. |
| 5,713,905 | A | 2/1998 | Goble et al. |
| 5,713,921 | A | 2/1998 | Bonutti |
| 5,716,359 | A | 2/1998 | Ojima et al. |
| 5,716,397 | A | 2/1998 | Myers |
| 5,718,717 | A | 2/1998 | Bonutti |
| 5,720,747 | A | 2/1998 | Burke |
| 5,720,765 | A | 2/1998 | Thal |
| 5,720,766 | A | 2/1998 | Zang et al. |
| 5,722,976 | A | 3/1998 | Brown |
| 5,725,549 | A | 3/1998 | Lam |
| 5,725,556 | A | 3/1998 | Moser et al. |
| 5,725,581 | A | 3/1998 | Brånemark et al. |
| 5,725,582 | A | 3/1998 | Bevan et al. |
| 5,726,722 | A | 3/1998 | Uehara et al. |
| 5,728,107 | A | 3/1998 | Zlock et al. |
| 5,728,109 | A | 3/1998 | Schulze et al. |
| 5,728,136 | A | 3/1998 | Thal |
| 5,733,293 | A | 3/1998 | Scirica et al. |
| 5,733,306 | A | 3/1998 | Bonutti |
| 5,733,307 | A | 3/1998 | Dinsdale |
| 5,735,875 | A | 4/1998 | Bonutti et al. |
| 5,741,259 | A | 4/1998 | Chan |
| 5,741,260 | A | 4/1998 | Songer et al. |
| 5,741,281 | A | 4/1998 | Martin et al. |
| 5,743,912 | A | 4/1998 | Lahille et al. |
| 5,746,751 | A | 5/1998 | Sherts |
| 5,746,752 | A | 5/1998 | Burkhart |
| 5,746,754 | A | 5/1998 | Chan |
| 5,749,898 | A | 5/1998 | Schulze et al. |
| 5,755,729 | A | 5/1998 | de la Torre et al. |
| 5,755,791 | A | 5/1998 | Whitson et al. |
| 5,766,176 | A | 6/1998 | Duncan |

| | | | | | |
|---|---|---|---|---|---|
| 5,766,218 A | 6/1998 | Arnott | 5,964,769 A | 10/1999 | Wagner et al. |
| 5,766,250 A | 6/1998 | Chervitz et al. | 5,964,783 A | 10/1999 | Grafton et al. |
| 5,769,894 A | 6/1998 | Ferragamo | 5,968,045 A | 10/1999 | Frazier |
| 5,769,899 A | 6/1998 | Schwartz et al. | 5,968,047 A | 10/1999 | Reed |
| 5,772,673 A | 6/1998 | Cuny et al. | 5,968,077 A | 10/1999 | Wojciechowicz et al. |
| 5,776,196 A | 7/1998 | Matsuzaki et al. | 5,972,006 A | 10/1999 | Sciaino, Jr. |
| 5,782,845 A | 7/1998 | Shewchuk | 5,976,125 A | 11/1999 | Graham |
| 5,782,862 A | 7/1998 | Bonutti | 5,976,127 A | 11/1999 | Lax |
| 5,782,864 A | 7/1998 | Lizardi | 5,980,524 A | 11/1999 | Justin et al. |
| 5,782,866 A | 7/1998 | Wenstrom, Jr. | 5,980,539 A | 11/1999 | Kontos |
| 5,785,714 A | 7/1998 | Morgan et al. | 5,980,558 A | 11/1999 | Wiley |
| 5,792,142 A | 8/1998 | Galitzer | 5,980,559 A | 11/1999 | Bonutti |
| 5,792,149 A | 8/1998 | Sherts et al. | 5,989,252 A | 11/1999 | Fumex |
| 5,796,127 A | 8/1998 | Hayafuji et al. | 5,989,256 A | 11/1999 | Kuslich et al. |
| 5,797,915 A | 8/1998 | Pierson, III et al. | 5,989,282 A | 11/1999 | Bonutti |
| 5,797,928 A | 8/1998 | Kogasaka et al. | 5,993,452 A | 11/1999 | Vandewalle |
| 5,800,407 A | 9/1998 | Eldor et al. | 5,993,476 A | 11/1999 | Groiso |
| 5,810,824 A | 9/1998 | Chan | 5,997,542 A | 12/1999 | Burke |
| 5,810,848 A | 9/1998 | Hayhurst | 5,997,552 A | 12/1999 | Person et al. |
| 5,814,069 A | 9/1998 | Schulze et al. | 5,997,575 A | 12/1999 | Whitson et al. |
| 5,814,070 A | 9/1998 | Borzone et al. | 6,001,100 A | 12/1999 | Sherman et al. |
| 5,814,072 A | 9/1998 | Bonutti | 6,007,538 A | 12/1999 | Levin |
| 5,814,073 A | 9/1998 | Bonutti | 6,007,567 A | 12/1999 | Bonutti |
| 5,823,980 A | 10/1998 | Kopfer | 6,010,525 A | 1/2000 | Bonutti et al. |
| 5,824,011 A | 10/1998 | Stone et al. | 6,016,727 A | 1/2000 | Morgan |
| 5,830,234 A | 11/1998 | Wojciechowicz et al. | 6,022,352 A | 2/2000 | Vandewalle |
| 5,843,084 A | 12/1998 | Hart et al. | 6,022,373 A | 2/2000 | Li |
| 5,845,645 A | 12/1998 | Bonutti | 6,024,758 A | 2/2000 | Thal |
| 5,846,254 A | 12/1998 | Schulze et al. | 6,027,523 A | 2/2000 | Schmieding |
| 5,848,983 A | 12/1998 | Basaj et al. | 6,030,410 A | 2/2000 | Zurbrugg |
| 5,849,012 A | 12/1998 | Abboudi | 6,033,429 A | 3/2000 | Magovern |
| 5,860,973 A | 1/1999 | Michelson | 6,033,430 A | 3/2000 | Bonutti |
| 5,868,740 A | 2/1999 | LeVeen et al. | 6,039,753 A | 3/2000 | Meislin |
| 5,868,748 A | 2/1999 | Burke | 6,041,485 A | 3/2000 | Pedlick et al. |
| 5,868,789 A | 2/1999 | Huebner | 6,042,601 A | 3/2000 | Smith |
| 5,871,484 A | 2/1999 | Spievack et al. | 6,045,551 A | 4/2000 | Bonutti |
| 5,871,486 A | 2/1999 | Huebner et al. | 6,045,571 A | 4/2000 | Hill et al. |
| 5,871,490 A | 2/1999 | Schulze et al. | 6,045,572 A | 4/2000 | Johnson et al. |
| 5,885,294 A | 3/1999 | Pedlick et al. | 6,045,573 A | 4/2000 | Wenstrom, Jr. et al. |
| 5,891,168 A | 4/1999 | Thal | 6,045,574 A | 4/2000 | Thal |
| 5,893,592 A | 4/1999 | Schulze et al. | 6,047,826 A | 4/2000 | Kalinski et al. |
| 5,895,395 A | 4/1999 | Yeung | 6,048,343 A | 4/2000 | Mathis et al. |
| 5,897,564 A | 4/1999 | Schulze et al. | 6,051,006 A | 4/2000 | Shluzas et al. |
| 5,897,574 A | 4/1999 | Bonutti | 6,051,007 A | 4/2000 | Hogendijk et al. |
| 5,899,902 A | 5/1999 | Brown et al. | 6,053,916 A | 4/2000 | Moore |
| 5,899,938 A | 5/1999 | Sklar et al. | 6,053,921 A | 4/2000 | Wagner et al. |
| 5,908,421 A | 6/1999 | Beger et al. | 6,056,752 A | 5/2000 | Roger et al. |
| 5,908,436 A | 6/1999 | Cuschieri et al. | 6,056,772 A | 5/2000 | Bonutti |
| 5,910,148 A | 6/1999 | Reimels et al. | 6,056,773 A | 5/2000 | Bonutti |
| 5,911,721 A | 6/1999 | Nicholson et al. | 6,059,817 A | 5/2000 | Bonutti et al. |
| 5,918,604 A | 7/1999 | Whelan | 6,059,818 A | 5/2000 | Johnson et al. |
| 5,921,986 A | 7/1999 | Bonutti | 6,062,344 A | 5/2000 | Okabe et al. |
| 5,925,008 A | 7/1999 | Douglas | 6,068,648 A | 5/2000 | Cole et al. |
| 5,928,231 A | 7/1999 | Klein et al. | 6,071,305 A | 6/2000 | Brown et al. |
| 5,928,267 A | 7/1999 | Bonutti et al. | 6,074,403 A | 6/2000 | Nord |
| RE36,289 E | 8/1999 | Le et al. | 6,077,277 A | 6/2000 | Mollenauer et al. |
| 5,931,838 A | 8/1999 | Vito | 6,077,292 A | 6/2000 | Bonutti |
| 5,931,844 A | 8/1999 | Thompson et al. | 6,080,185 A | 6/2000 | Johnson et al. |
| 5,931,869 A | 8/1999 | Boucher et al. | 6,086,591 A | 7/2000 | Bojarski |
| 5,935,119 A | 8/1999 | Guy et al. | 6,086,592 A | 7/2000 | Rosenberg et al. |
| 5,935,133 A | 8/1999 | Wagner et al. | 6,086,608 A | 7/2000 | Ek et al. |
| 5,935,149 A | 8/1999 | Ek | 6,093,200 A | 7/2000 | Liu et al. |
| 5,938,668 A | 8/1999 | Scirica et al. | 6,096,060 A | 8/2000 | Fitts et al. |
| 5,941,439 A | 8/1999 | Kammerer et al. | 6,099,527 A | 8/2000 | Hochschuler et al. |
| 5,941,900 A | 8/1999 | Bonutti | 6,099,530 A | 8/2000 | Simonian et al. |
| 5,944,739 A | 8/1999 | Zlock et al. | 6,099,568 A | 8/2000 | Simonian et al. |
| 5,946,783 A | 9/1999 | Plociennik et al. | 6,106,545 A | 8/2000 | Egan |
| 5,947,915 A | 9/1999 | Thibodo, Jr. | 6,110,128 A | 8/2000 | Andelin et al. |
| 5,947,982 A | 9/1999 | Duran | 6,117,160 A | 9/2000 | Bonutti |
| 5,947,999 A | 9/1999 | Groiso | 6,117,162 A | 9/2000 | Schmieding et al. |
| 5,948,002 A | 9/1999 | Bonutti | 6,123,710 A | 9/2000 | Pinczewski et al. |
| 5,951,559 A | 9/1999 | Burkhart | 6,132,433 A | 10/2000 | Whelan |
| 5,951,560 A | 9/1999 | Simon et al. | 6,132,437 A | 10/2000 | Omurtag et al. |
| 5,954,747 A | 9/1999 | Clark | 6,139,565 A | 10/2000 | Stone et al. |
| 5,957,953 A | 9/1999 | DiPoto et al. | RE36,974 E | 11/2000 | Bonutti |
| 5,961,521 A | 10/1999 | Roger et al. | 6,143,017 A | 11/2000 | Thal |
| 5,961,524 A | 10/1999 | Crombie | 6,146,406 A | 11/2000 | Shluzas et al. |
| 5,964,764 A | 10/1999 | West, Jr. et al. | 6,146,408 A | 11/2000 | Bartlett |
| 5,964,767 A | 10/1999 | Tapia et al. | 6,149,653 A | 11/2000 | Deslauriers |

| Patent No. | Kind | Date | Inventor |
|---|---|---|---|
| 6,149,669 | A | 11/2000 | Li |
| 6,152,928 | A | 11/2000 | Wenstrom, Jr. |
| 6,152,934 | A | 11/2000 | Harper et al. |
| 6,152,936 | A | 11/2000 | Christy et al. |
| 6,152,949 | A | 11/2000 | Bonutti |
| 6,156,039 | A | 12/2000 | Thal |
| 6,156,056 | A | 12/2000 | Kearns et al. |
| 6,159,234 | A | 12/2000 | Bonutti et al. |
| 6,165,203 | A | 12/2000 | Krebs |
| 6,168,598 | B1 | 1/2001 | Martello |
| 6,168,628 | B1 | 1/2001 | Huebner |
| 6,179,840 | B1 | 1/2001 | Bowman |
| 6,183,461 | B1 | 2/2001 | Matsuura et al. |
| 6,187,025 | B1 | 2/2001 | Machek |
| 6,190,401 | B1 | 2/2001 | Green et al. |
| 6,190,411 | B1 | 2/2001 | Lo et al. |
| 6,193,754 | B1 | 2/2001 | Seedhom et al. |
| 6,200,318 | B1 | 3/2001 | Har-Shai et al. |
| 6,200,329 | B1 | 3/2001 | Fung et al. |
| 6,200,330 | B1 | 3/2001 | Benderev et al. |
| 6,203,556 | B1 | 3/2001 | Evans et al. |
| 6,203,565 | B1 | 3/2001 | Bonutti et al. |
| 6,203,572 | B1 | 3/2001 | Johnson et al. |
| 6,206,883 | B1 | 3/2001 | Tunc |
| 6,210,376 | B1 | 4/2001 | Grayson |
| 6,214,012 | B1 | 4/2001 | Karpman et al. |
| 6,217,580 | B1 | 4/2001 | Levin |
| 6,221,107 | B1 | 4/2001 | Steiner et al. |
| 6,228,096 | B1 | 5/2001 | Marchand |
| 6,231,592 | B1 | 5/2001 | Bonutti et al. |
| 6,235,057 | B1 | 5/2001 | Roger et al. |
| 6,238,395 | B1 | 5/2001 | Bonutti |
| 6,241,734 | B1 | 6/2001 | Scribner et al. |
| 6,241,747 | B1 | 6/2001 | Ruff |
| 6,241,771 | B1 | 6/2001 | Gresser et al. |
| 6,245,081 | B1 | 6/2001 | Bowman et al. |
| 6,258,091 | B1 | 7/2001 | Sevrain et al. |
| 6,267,766 | B1 | 7/2001 | Burkhart |
| 6,269,716 | B1 | 8/2001 | Amis |
| 6,270,518 | B1 | 8/2001 | Pedlick et al. |
| 6,273,890 | B1 | 8/2001 | Frazier |
| 6,283,973 | B1 | 9/2001 | Hubbard et al. |
| 6,283,996 | B1 | 9/2001 | Chervitz et al. |
| 6,287,307 | B1 | 9/2001 | Abboudi |
| 6,287,325 | B1 | 9/2001 | Bonutti |
| 6,293,961 | B2 | 9/2001 | Schwartz et al. |
| 6,296,659 | B1 | 10/2001 | Foerster |
| 6,299,615 | B1 | 10/2001 | Huebner |
| 6,302,888 | B1 | 10/2001 | Mellinger et al. |
| 6,302,899 | B1 | 10/2001 | Johnson et al. |
| 6,306,156 | B1 | 10/2001 | Clark |
| 6,306,159 | B1 | 10/2001 | Schwartz et al. |
| 6,309,405 | B1 | 10/2001 | Bonutti |
| 6,312,448 | B1 | 11/2001 | Bonutti |
| 6,315,788 | B1 | 11/2001 | Roby |
| 6,319,271 | B1 | 11/2001 | Schwartz et al. |
| 6,328,758 | B1 | 12/2001 | Tornier et al. |
| 6,342,060 | B1 | 1/2002 | Adams |
| 6,343,531 | B2 | 2/2002 | Amis |
| 6,358,270 | B1 | 3/2002 | Lemer |
| 6,364,897 | B1 | 4/2002 | Bonutti |
| 6,368,322 | B1 | 4/2002 | Luks et al. |
| 6,368,326 | B1 | 4/2002 | Dakin et al. |
| 6,368,343 | B1 | 4/2002 | Bonutti et al. |
| 6,371,124 | B1 | 4/2002 | Whelan |
| 6,379,361 | B1 | 4/2002 | Beck, Jr. et al. |
| 6,383,190 | B1 | 5/2002 | Preissman |
| 6,383,199 | B2 | 5/2002 | Carter et al. |
| 6,387,113 | B1 | 5/2002 | Hawkins et al. |
| 6,387,129 | B2 | 5/2002 | Rieser et al. |
| 6,391,030 | B1 | 5/2002 | Wagner et al. |
| 6,398,785 | B2 | 6/2002 | Carchidi et al. |
| 6,406,479 | B1 | 6/2002 | Justin et al. |
| 6,409,743 | B1 | 6/2002 | Fenton, Jr. |
| 6,413,260 | B1 | 7/2002 | Berrevoets et al. |
| 6,423,088 | B1 | 7/2002 | Fenton, Jr. |
| 6,428,562 | B2 | 8/2002 | Bonutti |
| 6,432,123 | B2 | 8/2002 | Schwartz et al. |
| 6,436,123 | B1 | 8/2002 | Magovern |
| 6,436,124 | B1 | 8/2002 | Anderson et al. |
| 6,440,134 | B1 | 8/2002 | Zaccherotti et al. |
| 6,440,136 | B1 | 8/2002 | Gambale et al. |
| 6,447,516 | B1 | 9/2002 | Bonutti |
| 6,451,030 | B2 | 9/2002 | Li et al. |
| 6,454,768 | B1 | 9/2002 | Jackson |
| 6,458,134 | B1 | 10/2002 | Songer et al. |
| 6,461,373 | B2 | 10/2002 | Wyman et al. |
| 6,464,713 | B2 | 10/2002 | Bonutti |
| 6,468,293 | B2 | 10/2002 | Bonutti et al. |
| 6,471,707 | B1 | 10/2002 | Miller et al. |
| 6,475,230 | B1 | 11/2002 | Bonutti et al. |
| 6,482,210 | B1 | 11/2002 | Skiba et al. |
| 6,485,504 | B1 | 11/2002 | Johnson et al. |
| 6,497,901 | B1 | 12/2002 | Royer |
| 6,500,184 | B1 | 12/2002 | Chan et al. |
| 6,500,195 | B2 | 12/2002 | Bonutti |
| RE37,963 | E | 1/2003 | Thal |
| 6,503,267 | B2 | 1/2003 | Bonutti et al. |
| 6,506,190 | B1 | 1/2003 | Walshe |
| 6,508,820 | B2 | 1/2003 | Bales |
| 6,508,821 | B1 | 1/2003 | Schwartz et al. |
| 6,508,830 | B2 | 1/2003 | Steiner |
| 6,511,498 | B1 | 1/2003 | Fumex et al. |
| 6,511,499 | B2 | 1/2003 | Schmieding et al. |
| 6,517,542 | B1 | 2/2003 | Papay et al. |
| 6,517,552 | B1 | 2/2003 | Nord et al. |
| 6,517,578 | B2 | 2/2003 | Hein et al. |
| 6,517,579 | B1 | 2/2003 | Paulos et al. |
| 6,520,964 | B2 | 2/2003 | Tallarida et al. |
| 6,520,980 | B1 | 2/2003 | Foerster |
| 6,524,317 | B1 | 2/2003 | Ritchart et al. |
| 6,527,777 | B2 | 3/2003 | Justin |
| 6,527,794 | B1 | 3/2003 | McDevitt et al. |
| 6,527,795 | B1 | 3/2003 | Lizardi |
| 6,533,795 | B1 | 3/2003 | Tran et al. |
| 6,533,802 | B2 | 3/2003 | Bojarski et al. |
| 6,537,319 | B2 | 3/2003 | Whelan |
| 6,540,750 | B2 | 4/2003 | Burkhart |
| 6,540,769 | B1 | 4/2003 | Miller, III |
| 6,540,770 | B1 | 4/2003 | Tornier et al. |
| 6,544,281 | B2 | 4/2003 | ElAttrache et al. |
| 6,547,564 | B1 | 4/2003 | Hansson et al. |
| 6,547,800 | B2 | 4/2003 | Foerster et al. |
| 6,551,330 | B1 | 4/2003 | Bain et al. |
| 6,551,343 | B1 | 4/2003 | Tormala et al. |
| 6,553,802 | B1 | 4/2003 | Jacob et al. |
| 6,554,830 | B1 | 4/2003 | Chappius |
| 6,554,852 | B1 | 4/2003 | Oberlander |
| 6,554,862 | B2 | 4/2003 | Hays et al. |
| 6,562,071 | B2 | 5/2003 | Jarvinen et al. |
| 6,565,572 | B2 | 5/2003 | Chappius |
| 6,565,573 | B1 | 5/2003 | Ferrante et al. |
| 6,569,186 | B1 | 5/2003 | Winters et al. |
| 6,569,187 | B1 | 5/2003 | Bonutti et al. |
| 6,572,635 | B1 | 6/2003 | Bonutti |
| 6,575,925 | B1 | 6/2003 | Noble |
| 6,579,295 | B1 | 6/2003 | Supinski |
| 6,582,453 | B1 | 6/2003 | Tran et al. |
| 6,585,730 | B1 | 7/2003 | Foerster |
| 6,585,740 | B2 | 7/2003 | Schlapfer et al. |
| 6,585,750 | B2 | 7/2003 | Bonutti et al. |
| 6,589,245 | B1 | 7/2003 | Weiler et al. |
| 6,589,246 | B1 | 7/2003 | Hack et al. |
| 6,592,609 | B1 | 7/2003 | Bonutti |
| 6,595,911 | B2 | 7/2003 | LoVuolo |
| 6,599,289 | B1 | 7/2003 | Bojarski et al. |
| 6,605,096 | B1 | 8/2003 | Ritchart |
| 6,607,548 | B2 | 8/2003 | Pohjonen et al. |
| 6,610,079 | B1 | 8/2003 | Li et al. |
| 6,613,018 | B2 | 9/2003 | Bagga et al. |
| 6,616,694 | B1 | 9/2003 | Hart |
| 6,620,166 | B1 | 9/2003 | Wenstrom, Jr. et al. |
| 6,620,185 | B1 | 9/2003 | Harvie et al. |
| 6,620,195 | B2 | 9/2003 | Goble et al. |
| 6,620,329 | B2 | 9/2003 | Rosen et al. |
| 6,620,349 | B1 | 9/2003 | Lopez |
| 6,623,492 | B1 | 9/2003 | Berube et al. |
| 6,623,524 | B2 | 9/2003 | Schmieding |

| | | | | | | |
|---|---|---|---|---|---|---|
| 6,626,910 B1 | 9/2003 | Hugues et al. | | 6,986,781 B2 | 1/2006 | Smith |
| 6,626,919 B1 | 9/2003 | Swanstrom | | 6,989,034 B2 | 1/2006 | Hammer et al. |
| 6,629,977 B1 | 10/2003 | Wolf | | 7,001,429 B2 | 2/2006 | Ferguson |
| 6,635,073 B2 | 10/2003 | Bonutti | | 7,004,959 B2 | 2/2006 | Bonutti |
| 6,638,279 B2 | 10/2003 | Bonutti | | 7,048,754 B2 | 5/2006 | Martin et al. |
| 6,638,312 B2 | 10/2003 | Plouhar et al. | | 7,052,499 B2 | 5/2006 | Steger et al. |
| 6,641,596 B1 | 11/2003 | Lizardi | | 7,066,942 B2 | 6/2006 | Treace |
| 6,641,597 B2 | 11/2003 | Burkhart et al. | | 7,066,944 B2 | 6/2006 | Laufer et al. |
| 6,645,227 B2 | 11/2003 | Fallin et al. | | 7,081,126 B2 | 7/2006 | McDevitt et al. |
| 6,652,450 B2 | 11/2003 | Neisz et al. | | 7,087,064 B1 | 8/2006 | Hyde |
| 6,652,562 B2 | 11/2003 | Collier et al. | | 7,105,010 B2 | 9/2006 | Hart et al. |
| 6,652,563 B2 | 11/2003 | Dreyfuss | | 7,112,221 B2 | 9/2006 | Harris et al. |
| 6,656,182 B1 | 12/2003 | Hayhurst | | 7,118,583 B2 | 10/2006 | O'Quinn et al. |
| 6,656,183 B2 | 12/2003 | Colleran et al. | | 7,131,467 B2 | 11/2006 | Gao et al. |
| 6,658,182 B1 | 12/2003 | Gonthier et al. | | 7,137,996 B2 | 11/2006 | Steiner et al. |
| 6,660,008 B1 | 12/2003 | Foerster et al. | | 7,141,066 B2 | 11/2006 | Steiner et al. |
| 6,660,022 B1 | 12/2003 | Li et al. | | 7,144,414 B2 | 12/2006 | Harvie et al. |
| 6,663,634 B2 | 12/2003 | Ahrens et al. | | 7,153,127 B2 | 12/2006 | Struble et al. |
| 6,663,656 B2 | 12/2003 | Schmieding et al. | | 7,153,307 B2 | 12/2006 | Scribner et al. |
| 6,666,868 B2 | 12/2003 | Fallin | | 7,153,312 B1 | 12/2006 | Torrie et al. |
| 6,682,533 B1 | 1/2004 | Dinsdale et al. | | 7,153,327 B1 | 12/2006 | Metzger |
| 6,682,549 B2 | 1/2004 | Bartlett | | 7,160,333 B2 | 1/2007 | Plouhar et al. |
| 6,685,728 B2 | 2/2004 | Sinnott et al. | | 7,201,722 B2 | 4/2007 | Krueger |
| 6,689,137 B2 | 2/2004 | Reed | | 7,255,675 B2 | 8/2007 | Gertner et al. |
| 6,689,153 B1 | 2/2004 | Skiba | | 7,255,715 B2 | 8/2007 | Metzger |
| 6,689,154 B2 | 2/2004 | Bartlett | | 7,261,716 B2 | 8/2007 | Strobel et al. |
| 6,692,499 B2 | 2/2004 | Tormala et al. | | 7,264,634 B2 | 9/2007 | Schmieding |
| 6,712,849 B2 | 3/2004 | Re et al. | | 7,285,124 B2 | 10/2007 | Foerster |
| 6,716,224 B2 | 4/2004 | Singhatat | | 7,303,577 B1 | 12/2007 | Dean |
| 6,716,957 B2 | 4/2004 | Tunc | | 7,306,417 B2 | 12/2007 | Dorstewitz |
| 6,730,092 B2 | 5/2004 | Songer | | 7,326,222 B2 | 2/2008 | Dreyfuss et al. |
| 6,730,124 B2 | 5/2004 | Steiner | | 7,361,179 B2 | 4/2008 | Rousseau et al. |
| 6,736,799 B1 | 5/2004 | Erbe et al. | | 7,377,845 B2 | 5/2008 | Stewart et al. |
| 6,737,053 B1 | 5/2004 | Goh et al. | | 7,390,329 B2 | 6/2008 | Westra et al. |
| 6,746,483 B1 | 6/2004 | Bojarski et al. | | 7,390,332 B2 | 6/2008 | Selvitelli et al. |
| 6,752,810 B1 | 6/2004 | Gao et al. | | 7,399,018 B1 | 7/2008 | Khachaturian |
| 6,752,831 B2 | 6/2004 | Sybert et al. | | 7,442,210 B2 | 10/2008 | Segal et al. |
| 6,755,836 B1 | 6/2004 | Lewis | | 7,465,308 B2 | 12/2008 | Sikora et al. |
| 6,761,739 B2 | 7/2004 | Shepard | | 7,494,506 B2 | 2/2009 | Brulez et al. |
| 6,767,037 B2 | 7/2004 | Wenstrom, Jr. | | 7,513,910 B2 | 4/2009 | Buskirk et al. |
| 6,770,076 B2 | 8/2004 | Foerster | | 7,578,825 B2 | 8/2009 | Huebner |
| 6,770,084 B1 | 8/2004 | Bain et al. | | 7,585,311 B2 | 9/2009 | Green et al. |
| 6,773,450 B2 | 8/2004 | Leung et al. | | 7,601,165 B2 | 10/2009 | Stone |
| 6,779,701 B2 | 8/2004 | Bailly et al. | | 7,608,098 B1 | 10/2009 | Stone et al. |
| 6,780,190 B2 | 8/2004 | Maroney | | 7,615,076 B2 | 11/2009 | Cauthen, III et al. |
| 6,780,198 B1 | 8/2004 | Gregoire et al. | | 7,632,287 B2 | 12/2009 | Baker et al. |
| 6,802,862 B1 | 10/2004 | Roger et al. | | 7,651,509 B2 | 1/2010 | Bojarski et al. |
| 6,808,502 B2 | 10/2004 | Nguyen et al. | | 7,658,750 B2 | 2/2010 | Li |
| 6,808,526 B1 | 10/2004 | Magerl et al. | | 7,658,751 B2 | 2/2010 | Stone et al. |
| 6,814,741 B2 | 11/2004 | Bowman et al. | | 7,670,279 B2 | 3/2010 | Gertner |
| 6,830,572 B2 | 12/2004 | McDevitt et al. | | 7,678,123 B2 | 3/2010 | Chanduszko |
| 6,833,005 B1 | 12/2004 | Mantas et al. | | 7,695,493 B2 | 4/2010 | Saadat et al. |
| 6,840,953 B2 | 1/2005 | Martinek | | 7,736,379 B2 | 6/2010 | Ewers et al. |
| 6,860,885 B2 | 3/2005 | Bonutti | | 7,758,594 B2 | 7/2010 | Lamson et al. |
| 6,863,671 B1 | 3/2005 | Strobel et al. | | 7,776,041 B1 | 8/2010 | Walters |
| 6,872,040 B2 | 3/2005 | Deeg et al. | | 7,819,895 B2 | 10/2010 | Ginn et al. |
| 6,872,210 B2 | 3/2005 | Hearn | | 7,875,058 B2 | 1/2011 | Holmes, Jr. |
| 6,875,216 B2 | 4/2005 | Wolf | | 7,981,140 B2 | 7/2011 | Burkhart |
| 6,884,249 B2 | 4/2005 | May et al. | | 8,062,334 B2 | 11/2011 | Green et al. |
| 6,887,259 B2 | 5/2005 | Lizardi | | 2001/0010005 A1 | 7/2001 | Kammerer et al. |
| 6,890,354 B2 | 5/2005 | Steiner et al. | | 2001/0014825 A1 | 8/2001 | Burke et al. |
| 6,893,448 B2 | 5/2005 | O'Quinn et al. | | 2001/0019649 A1 | 9/2001 | Field et al. |
| 6,896,686 B2 | 5/2005 | Weber | | 2001/0037131 A1 | 11/2001 | Schmieding et al. |
| 6,899,722 B2 | 5/2005 | Bonutti | | 2001/0037153 A1 | 11/2001 | Rockwood et al. |
| 6,902,573 B2 | 6/2005 | Strobel et al. | | 2001/0041916 A1 | 11/2001 | Bonutti |
| 6,905,513 B1 | 6/2005 | Metzger | | 2001/0041937 A1 | 11/2001 | Rieser et al. |
| 6,908,466 B1 | 6/2005 | Bonutti et al. | | 2001/0041938 A1 | 11/2001 | Hein |
| 6,916,292 B2 | 7/2005 | Morawski et al. | | 2001/0044639 A1 | 11/2001 | Levinson |
| 6,916,321 B2 | 7/2005 | TenHuisen et al. | | 2001/0047206 A1 | 11/2001 | Sklar et al. |
| 6,921,402 B2 | 7/2005 | Contiliano et al. | | 2001/0051816 A1 | 12/2001 | Enzerink et al. |
| 6,923,823 B1 | 8/2005 | Bartlett et al. | | 2001/0053934 A1 | 12/2001 | Schmieding |
| 6,923,824 B2 | 8/2005 | Morgan et al. | | 2002/0001964 A1 | 1/2002 | Choi |
| 6,951,565 B2 | 10/2005 | Keane et al. | | 2002/0004669 A1 | 1/2002 | Bartlett |
| 6,966,887 B1 | 11/2005 | Chin | | 2002/0007182 A1 | 1/2002 | Kim |
| 6,966,916 B2 | 11/2005 | Kumar | | 2002/0010513 A1 | 1/2002 | Schmieding |
| 6,969,391 B1 | 11/2005 | Gazzani | | 2002/0013607 A1 | 1/2002 | Lemer |
| 6,969,398 B2 | 11/2005 | Stevens et al. | | 2002/0013608 A1 | 1/2002 | ElAttrache et al. |
| 6,972,027 B2 | 12/2005 | Fallin et al. | | 2002/0019649 A1 | 2/2002 | Sikora et al. |
| 6,980,903 B2 | 12/2005 | Daniels et al. | | 2002/0029066 A1 | 3/2002 | Foerster |

| | | |
|---|---|---|
| 2002/0032465 A1 | 3/2002 | Lemer |
| 2002/0055780 A1 | 5/2002 | Sklar |
| 2002/0058966 A1 | 5/2002 | Tormala et al. |
| 2002/0077659 A1 | 6/2002 | Johnson et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0161401 A1 | 10/2002 | Steiner |
| 2002/0161439 A1 | 10/2002 | Strobel et al. |
| 2002/0165548 A1 | 11/2002 | Jutley |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0188298 A1 | 12/2002 | Chan |
| 2002/0193830 A1 | 12/2002 | Bonutti |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1 | 6/2003 | Eichhorn et al. |
| 2003/0120309 A1 | 6/2003 | Colleran et al. |
| 2003/0130694 A1 | 7/2003 | Bojarski et al. |
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208210 A1 | 11/2003 | Dreyfuss et al. |
| 2003/0212456 A1 | 11/2003 | Lipchitz et al. |
| 2003/0220660 A1 | 11/2003 | Kortenbach et al. |
| 2003/0225459 A1 | 12/2003 | Hammer et al. |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0024457 A1 | 2/2004 | Boyce et al. |
| 2004/0044391 A1 | 3/2004 | Porter |
| 2004/0059357 A1 | 3/2004 | Koseki |
| 2004/0087981 A1 | 5/2004 | Berube et al. |
| 2004/0092936 A1 | 5/2004 | Miller et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0133206 A1 | 7/2004 | Stevens et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0182968 A1 | 9/2004 | Gentry |
| 2004/0187314 A1 | 9/2004 | Johnson |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243235 A1 | 12/2004 | Goh et al. |
| 2004/0249394 A1 | 12/2004 | Morris et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2005/0021087 A1 | 1/2005 | Koseki |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0070928 A1 | 3/2005 | Heino et al. |
| 2005/0074495 A1 | 4/2005 | Schwartz et al. |
| 2005/0085819 A1 | 4/2005 | Ellis et al. |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125036 A1 | 6/2005 | Roby |
| 2005/0125073 A1 | 6/2005 | Orban et al. |
| 2005/0131413 A1 | 6/2005 | O'Driscoll et al. |
| 2005/0137600 A1 | 6/2005 | Jacobs et al. |
| 2005/0137624 A1 | 6/2005 | Fallman |
| 2005/0149033 A1 | 7/2005 | McGuire et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251208 A1 | 11/2005 | Elmer et al. |
| 2005/0251210 A1 | 11/2005 | Westra et al. |
| 2005/0267479 A1 | 12/2005 | Morgan et al. |
| 2005/0267533 A1 | 12/2005 | Gertner |
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |

| | | | | | | |
|---|---|---|---|---|---|---|
| 2005/0283158 A1 | 12/2005 | West | | 2008/0065114 A1 | 3/2008 | Stone et al. |
| 2005/0283192 A1 | 12/2005 | Torrie et al. | | 2008/0071299 A1 | 3/2008 | Allinniemi et al. |
| 2006/0004410 A1 | 1/2006 | Nobis et al. | | 2008/0082101 A1 | 4/2008 | Reisberg |
| 2006/0015103 A1 | 1/2006 | Burke | | 2008/0082127 A1 | 4/2008 | Stone et al. |
| 2006/0015106 A1 | 1/2006 | Lerch et al. | | 2008/0082128 A1 | 4/2008 | Stone |
| 2006/0030884 A1 | 2/2006 | Yeung et al. | | 2008/0119892 A1 | 5/2008 | Brailovski et al. |
| 2006/0030948 A1 | 2/2006 | Manrique et al. | | 2008/0132753 A1 | 6/2008 | Goddard |
| 2006/0036265 A1 | 2/2006 | Dant | | 2008/0132932 A1 | 6/2008 | Hoeppner et al. |
| 2006/0052818 A1 | 3/2006 | Drake et al. | | 2008/0140092 A1 | 6/2008 | Stone et al. |
| 2006/0064125 A1 | 3/2006 | Henderson et al. | | 2008/0140093 A1 | 6/2008 | Stone et al. |
| 2006/0064126 A1 | 3/2006 | Fallin et al. | | 2008/0140128 A1 | 6/2008 | Smisson et al. |
| 2006/0069334 A1 | 3/2006 | Moskowitz | | 2008/0161852 A1 | 7/2008 | Kaiser et al. |
| 2006/0084943 A1 | 4/2006 | Rosenman et al. | | 2008/0161861 A1 | 7/2008 | Huebner |
| 2006/0085000 A1 | 4/2006 | Mohr et al. | | 2008/0172097 A1 | 7/2008 | Lerch et al. |
| 2006/0089672 A1 | 4/2006 | Martinek | | 2008/0188933 A1 | 8/2008 | Koob et al. |
| 2006/0100627 A1 | 5/2006 | Stone et al. | | 2008/0188936 A1 | 8/2008 | Ball et al. |
| 2006/0100637 A1 | 5/2006 | Rathbun et al. | | 2008/0221527 A1 | 9/2008 | Bradley et al. |
| 2006/0111721 A1 | 5/2006 | Puricelli et al. | | 2008/0221578 A1 | 9/2008 | Zeitani |
| 2006/0116685 A1 | 6/2006 | Urbanski et al. | | 2008/0255613 A1 | 10/2008 | Kaiser et al. |
| 2006/0121084 A1 | 6/2006 | Borden et al. | | 2008/0262544 A1 | 10/2008 | Burkhart |
| 2006/0122611 A1 | 6/2006 | Morales et al. | | 2008/0268064 A1 | 10/2008 | Woodell-May |
| 2006/0135958 A1 | 6/2006 | Marissen et al. | | 2008/0269674 A1 | 10/2008 | Stone |
| 2006/0149266 A1 | 7/2006 | Cordasco | | 2008/0275477 A1 | 11/2008 | Sterrett et al. |
| 2006/0161161 A1 | 7/2006 | Shifrin et al. | | 2008/0312689 A1 | 12/2008 | Denham et al. |
| 2006/0167458 A1 | 7/2006 | Gabele | | 2009/0018589 A1 | 1/2009 | Smisson, III et al. |
| 2006/0167481 A1 | 7/2006 | Baker et al. | | 2009/0018655 A1 | 1/2009 | Brunelle et al. |
| 2006/0167482 A1 | 7/2006 | Swain et al. | | 2009/0054928 A1 | 2/2009 | Denham et al. |
| 2006/0178680 A1 | 8/2006 | Nelson et al. | | 2009/0062854 A1 | 3/2009 | Kaiser et al. |
| 2006/0189993 A1 | 8/2006 | Stone | | 2009/0082790 A1 | 3/2009 | Shad et al. |
| 2006/0190042 A1 | 8/2006 | Stone et al. | | 2009/0082805 A1 | 3/2009 | Kaiser et al. |
| 2006/0195101 A1 | 8/2006 | Stevens | | 2009/0099598 A1 | 4/2009 | McDevitt et al. |
| 2006/0200235 A1 | 9/2006 | Bianchi et al. | | 2009/0105754 A1 | 4/2009 | Sethi |
| 2006/0229671 A1 | 10/2006 | Steiner et al. | | 2009/0118774 A1 | 5/2009 | Miller, III |
| 2006/0241624 A1 | 10/2006 | Kizuka et al. | | 2009/0118775 A1 | 5/2009 | Burke |
| 2006/0247642 A1 | 11/2006 | Stone et al. | | 2009/0125073 A1 | 5/2009 | Rehm |
| 2006/0253130 A1 | 11/2006 | Wolniewicz | | 2009/0138002 A1 | 5/2009 | Fenton |
| 2006/0259048 A1 | 11/2006 | Koseki | | 2009/0138054 A1 | 5/2009 | Teague et al. |
| 2006/0271192 A1 | 11/2006 | Olsen et al. | | 2009/0156997 A1 | 6/2009 | Trenhaile |
| 2006/0276793 A1 | 12/2006 | Berry | | 2009/0163949 A1 | 6/2009 | Rolnick et al. |
| 2006/0276809 A1 | 12/2006 | Oliveira | | 2009/0177233 A1 | 7/2009 | Malek |
| 2006/0280768 A1 | 12/2006 | Hwang et al. | | 2009/0192468 A1 | 7/2009 | Stone |
| 2006/0282082 A1 | 12/2006 | Fanton et al. | | 2009/0198277 A1 | 8/2009 | Gordon et al. |
| 2006/0282085 A1 | 12/2006 | Stone et al. | | 2009/0204146 A1 | 8/2009 | Kaiser et al. |
| 2006/0293709 A1 | 12/2006 | Bojarski et al. | | 2009/0228042 A1 | 9/2009 | Koogle, Jr. et al. |
| 2007/0005080 A1 | 1/2007 | Wolniewicz et al. | | 2009/0234357 A1 | 9/2009 | Morales et al. |
| 2007/0016305 A1 | 1/2007 | Chudik | | 2009/0234358 A1 | 9/2009 | Morales et al. |
| 2007/0021779 A1 | 1/2007 | Garvin et al. | | 2009/0240251 A1 | 9/2009 | Gabele |
| 2007/0032800 A1 | 2/2007 | Ortiz et al. | | 2009/0248091 A1 | 10/2009 | Teague et al. |
| 2007/0038218 A1 | 2/2007 | Grevious | | 2009/0265014 A1 | 10/2009 | May et al. |
| 2007/0043371 A1 | 2/2007 | Teague et al. | | 2009/0306711 A1 | 12/2009 | Stone et al. |
| 2007/0055249 A1 | 3/2007 | Jensen et al. | | 2009/0312776 A1 | 12/2009 | Kaiser et al. |
| 2007/0055251 A1 | 3/2007 | Huebner et al. | | 2009/0318960 A1 | 12/2009 | Burkhart |
| 2007/0055255 A1 | 3/2007 | Siegel | | 2009/0318961 A1 | 12/2009 | Stone et al. |
| 2007/0060922 A1 | 3/2007 | Dreyfuss | | 2010/0042114 A1 | 2/2010 | Schaffhausen |
| 2007/0067025 A1 | 3/2007 | Schwartz | | 2010/0087857 A1 | 4/2010 | Stone et al. |
| 2007/0073307 A1 | 3/2007 | Scribner et al. | | 2010/0145384 A1 | 6/2010 | Stone et al. |
| 2007/0078435 A1 | 4/2007 | Stone et al. | | 2010/0191342 A1 | 7/2010 | Byrd et al. |
| 2007/0083236 A1 | 4/2007 | Sikora et al. | | 2010/0211075 A1 | 8/2010 | Stone |
| 2007/0093847 A1 | 4/2007 | Scribner et al. | | 2010/0256677 A1 | 10/2010 | Albertorio et al. |
| 2007/0100350 A1 | 5/2007 | Deffenbaugh et al. | | 2010/0268273 A1 | 10/2010 | Albertorio et al. |
| 2007/0118217 A1 | 5/2007 | Brulez et al. | | 2010/0268275 A1 | 10/2010 | Stone et al. |
| 2007/0123883 A1 | 5/2007 | Ellis et al. | | 2010/0270306 A1 | 10/2010 | Shiffer |
| 2007/0142838 A1 | 6/2007 | Jordan | | 2010/0292792 A1 | 11/2010 | Stone et al. |
| 2007/0156174 A1 | 7/2007 | Kaiser et al. | | 2010/0305698 A1 | 12/2010 | Metzger et al. |
| 2007/0162018 A1 | 7/2007 | Jensen et al. | | 2010/0305709 A1 | 12/2010 | Metzger et al. |
| 2007/0185488 A1 | 8/2007 | Pohjonen et al. | | 2010/0312341 A1 | 12/2010 | Kaiser et al. |
| 2007/0185532 A1 | 8/2007 | Stone et al. | | 2011/0087284 A1 | 4/2011 | Stone et al. |
| 2007/0191849 A1 | 8/2007 | ElAttrache et al. | | 2011/0098727 A1 | 4/2011 | Kaiser et al. |
| 2007/0191853 A1 | 8/2007 | Stone | | 2011/0106153 A1 | 5/2011 | Stone et al. |
| 2007/0219558 A1 | 9/2007 | Deutsch | | 2011/0160767 A1 | 6/2011 | Stone et al. |
| 2007/0239209 A1 | 10/2007 | Fallman | | 2011/0160768 A1 | 6/2011 | Stone et al. |
| 2007/0239275 A1 | 10/2007 | Willobee | | 2011/0208239 A1 | 8/2011 | Stone et al. |
| 2007/0250163 A1 | 10/2007 | Cassani | | 2011/0208240 A1 | 8/2011 | Stone et al. |
| 2007/0260251 A1 | 11/2007 | Weier et al. | | 2011/0213416 A1 | 9/2011 | Kaiser |
| 2007/0260279 A1 | 11/2007 | Hotter et al. | | 2011/0218625 A1 | 9/2011 | Berelsman et al. |
| 2007/0270856 A1 | 11/2007 | Morales et al. | | 2011/0224799 A1 | 9/2011 | Stone |
| 2007/0276387 A1 | 11/2007 | Morales et al. | | 2011/0264141 A1 | 10/2011 | Denham et al. |
| 2008/0027446 A1 | 1/2008 | Stone et al. | | 2011/0270278 A1 | 11/2011 | Overes et al. |
| 2008/0046009 A1 | 2/2008 | Albertorio et al. | | 2011/0270306 A1 | 11/2011 | Denham et al. |

| | | |
|---|---|---|
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0059418 A1 | 3/2012 | Denham et al. |

FOREIGN PATENT DOCUMENTS

| | | |
|---|---|---|
| AU | 440266 | 10/1967 |
| AU | 2223767 | 11/1968 |
| AU | 5028569 | 8/1970 |
| AU | 5850469 | 1/1971 |
| AU | 5963869 | 2/1971 |
| AU | 1505470 | 11/1971 |
| AU | 3615171 | 5/1973 |
| AU | 7110887 | 10/1987 |
| AU | 639410 | 11/1989 |
| AU | 651929 | 8/1994 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 | 2/1986 |
| DE | 4127550 | 2/1993 |
| DE | 4302397 | 7/1993 |
| DE | 29621340 | 5/1998 |
| DE | 19841252 | 3/2000 |
| EP | 0108912 | 5/1984 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0440991 | 8/1991 |
| EP | 0441065 | 8/1991 |
| EP | 0451932 | 10/1991 |
| EP | 0464480 | 1/1992 |
| EP | 0497079 | 8/1992 |
| EP | 0502509 | 9/1992 |
| EP | 0502698 | 9/1992 |
| EP | 520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 | 5/1994 |
| EP | 0611551 A1 | 8/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| FR | 2622790 | 5/1989 |
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2227175 | 7/1990 |
| GB | 2253147 | 9/1992 |
| GB | 2312376 | 10/1997 |
| GB | 2403416 A | 1/2005 |
| JP | 5362911 | 5/1978 |
| JP | 5362912 | 5/1978 |
| JP | 5374942 | 6/1978 |
| JP | 5378230 | 6/1978 |
| JP | 62159647 | 7/1987 |
| JP | 62295657 | 12/1987 |
| JP | 5269160 | 10/1993 |
| JP | 5300917 | 11/1993 |
| JP | 751292 | 2/1995 |
| JP | 10211213 | 8/1998 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9944544 | 9/1999 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-2004091412 A1 | 10/2004 |
| WO | WO-2005104992 | 11/2005 |
| WO | WO-2009012021 A1 | 1/2009 |

OTHER PUBLICATIONS

"Make your next tendon repair an open-and-shut case. The Teno Fix® Tendon Repair System", Teno Fix® brochure, 2003 (2 pages) Ortheon® Medical.

Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.

"Arthroscopic Meniscal Repair using the Meniscal Cinch™", Surgical Technique brochure. (2008) Arthrex® 6 sheets.

Pioneer® Sternal Cable System (2010).

Rapid Sternal Closure (2006) KLS Martin L.P. http://www.rapidsternalclosure.com/medical/demo.php Web accessed Sep. 8, 2008.

Saxena, Pankaj, MCh, DNB et al., "Use of Double Wires in Sternal Closure, A Useful Technique," Texas Heart® Institute. Journal List>Tex Heart Inst J > v.33(4); (2006).

Zeitani, Jacob, M.D., "A New Sternal Reinforcement Device to Prevent and Treat Sternal Dehiscence," CTSNet.org (Jun. 30, 2008).

"AperFix® System Surgical Technique Guide. Single Tunnel Double Bundle.™" Cayenne Medical brochure. (Aug. 2008) 8 sheets.

"Bio-Intrafix Tibial Soft Tissue Fasteners, Building on the Legacy of IntraFix," brochure. DePuy Mitek,(Feb. 2007) 6 sheets.

"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.

"JuggerKnot™ Soft Anchor Midfoot Repair," brochure. Biomet Sports Medicine (Jul. 2011) 12 sheets.

"JuggerKnot™ Soft Anchor. It's Small. It's strong. And it's all suture . . . " Ordering Information brochure. Biomet Sports Medicine (Jun. 2011) 2 sheets.

"JuggerKnot™ Soft Anchor. Labral Repair," brochure. Biomet Sports Medicine (Apr. 2011) 12 sheets.

International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.

International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.

Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.

US 6,238,428, 05/2001, Schwartz et al. (withdrawn).

"EZ Loc Femoral Fixation Device," copyright 2005 Arthrotek, Inc. (8 sheets).

"PANALOK Anchor with PDS II and ETHIBOND Suture", Mitek Products ETHICON, 1997.

"SE Graft Tensioning System Surgical Technique," Linvatec Corporation copyright 2003, 2004.

"Technique for ACL Reconstruction with Acufex Director Drill Guide and Endobutton CL," by Thomas D. Roseberg, copyright 1999 Smith & Nephew.

A. Weiler, et al; Biodegradierbare Interferenzschrauben in der Kreuzbandchirurgie; OP-Journal 14 pp. 278-284; 1998.

Arthrotek, A Biomet Company; Knees; Sure fire Hybrid Meniscal Device.

Arthrotek, A Biomet Company; Sure fire Hybrid Meniscal Device; Launch Date: Fall AANA 2004.

Bio-Intrafix (TCP/PLA & Intrafix, Tibial Soft Tissue Fasteners, by DePuy Mitek, 6 sheets, (date unknown).

F. Alan Barber, M.D., "Uses and Abuses of Sutures and Anchors," Shoulder Scope, San Diego Shoulder Arthroscopy Library.

F. Alan Barber, M.D., "Using Sutures and Anchors," San Diego Shoulder Arthroscopy Course, 17th Annual Meeting.

Flavia Namie Azato, et al. "Traction endurance biomechanical study of metallic suture anchors at different insertion angles," Acta ortop. bras., vol. 11, No. 1, Sao Paulo, Jan./Mar. 2003.

Hecker AT, et al., "Pull-out strength of suture anchors for rotator cuff and Bankart lesion repairs," Am J Sports Med. 1993.

Lawhorn, M.D., Keith, MaxFire™ Meniscal Repair Device with Zip Loop™ Technology, Biomet Sports Medicine, Feb. 29, 2008.

Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.

Opus Medical; The AutoCuff System; www.opusmedical.com; 2003.

Patrick Hunt, et al.; Development of a Perforated Biodegradable Interference Screw; Arthroscopy: The Journal of Arthroscopic and Related Surgery, vol. 21, No. 3; pp. 258-265; Mar. 2005.

Roy Alan Majors, M.D.; "Meniscal repairs: proven techniques and current trends," Lippincott Williams & Wilkins, Inc.; 2002.

Shoulder Arthroscopy; pp. H-2-H-22.

Smith & Nephew Endoscopy, "Endoscopic Meniscal Repair Using the T-Fix;" 1996.

Smith & Nephew, "Fast-Fix," Meniscal Repair System; 2001.

Stuart E. Fromm, M.D., RapidLoc, Meniscal Repair System, Mitek Products, Ethicon, 2001.

ToggleLoc™ Femoral Fixation Device, Arthrotek, Mar. 31, 2006.

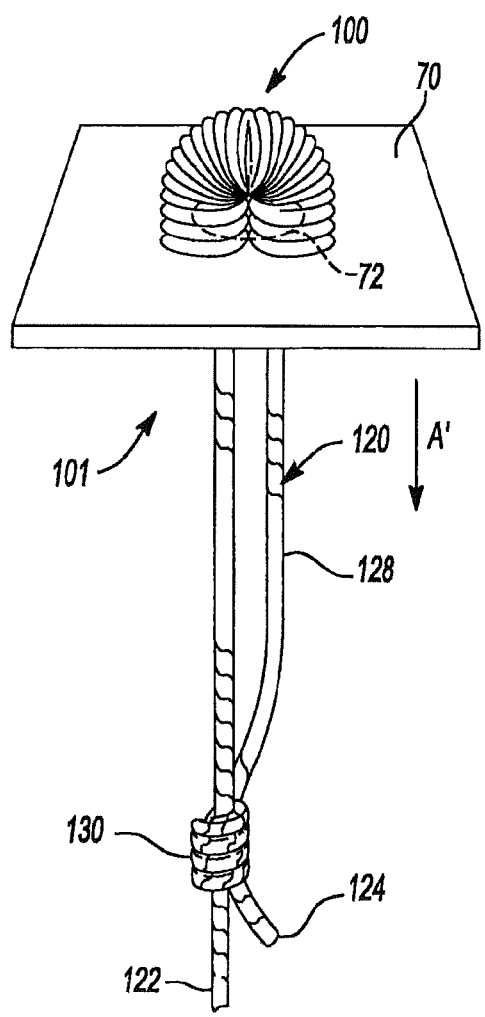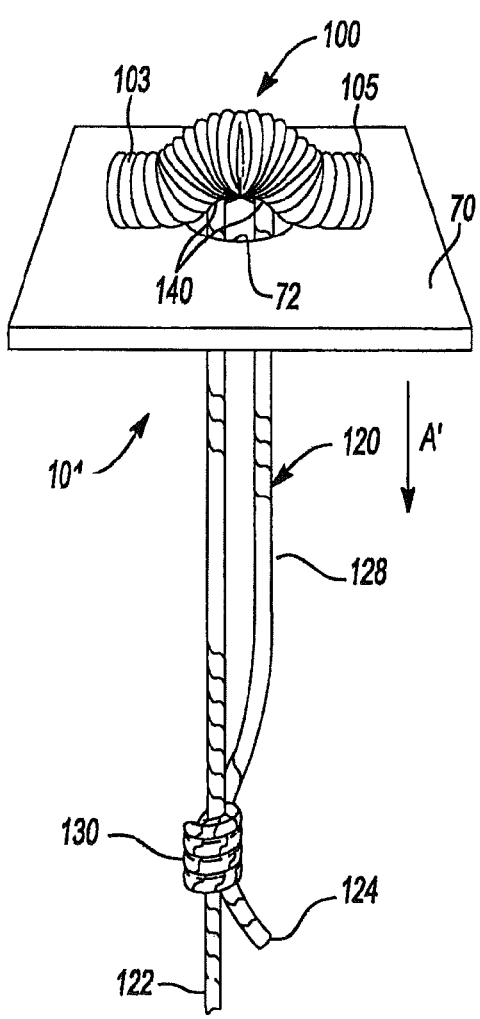

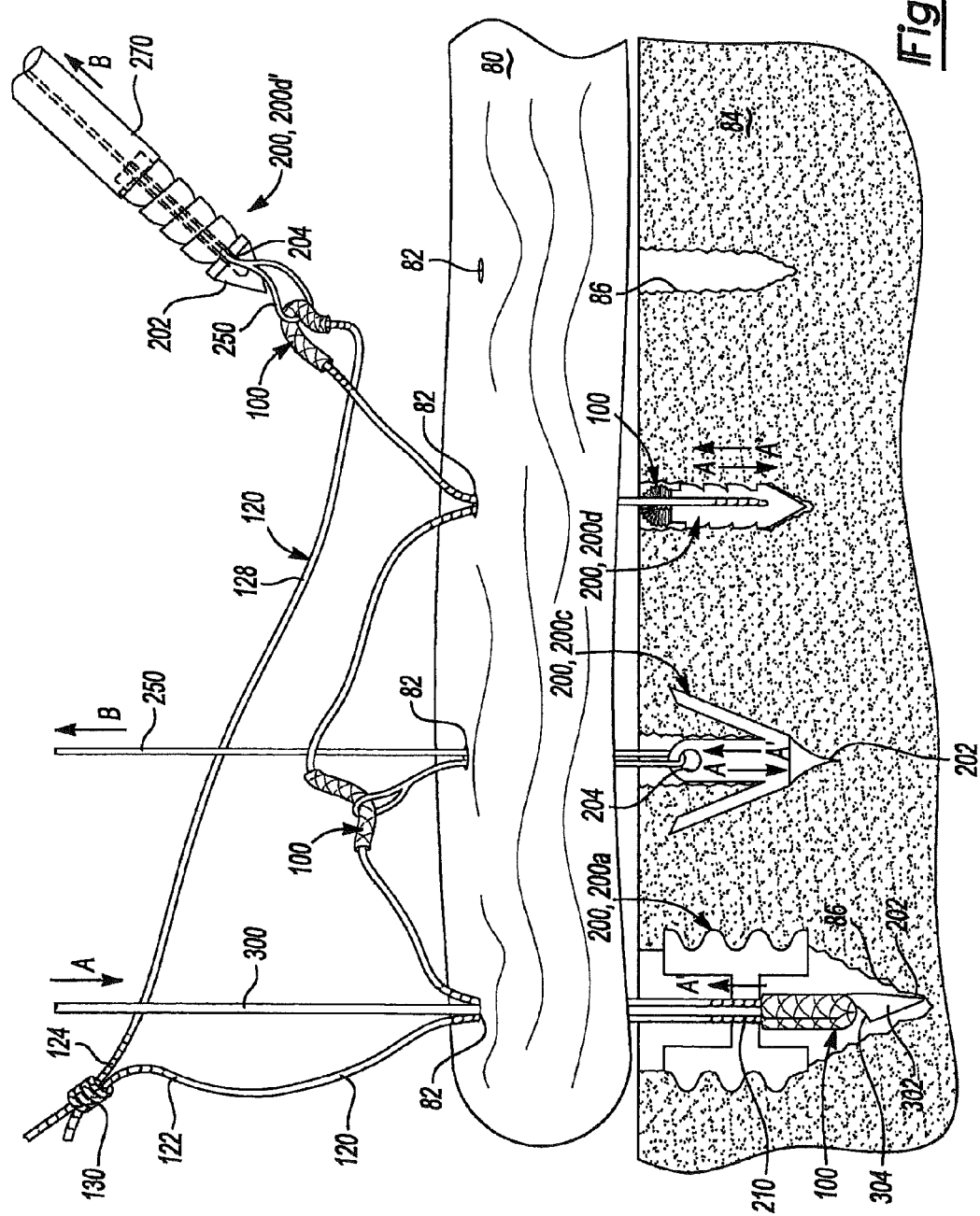

METHOD FOR TISSUE FIXATION

CROSS-REFERENCE TO RELATED APPLICATIONS

This application is a continuation-in-part application of U.S. patent application Ser. No. 12/474,802 filed on May 29, 2009, now U.S. Pat. No. 8,088,130 issued Jan. 3, 2012, and is a continuation-in-part application of U.S. patent application Ser. No. 11/541,506 filed on Sep. 29, 2006, now U.S. Pat. No. 7,601,165 issued Oct. 13, 2009, and is a continuation-in-part application of U.S. patent application Ser. No. 11/541,505 filed on Sep. 29, 2006, now U.S. Pat. No. 7,658,751 issued Feb. 9, 2010, and is a continuation-in-part application of U.S. patent application Ser. No. 12/014,399 filed on Jan. 15, 2008, now U.S. Pat. No. 7,909,851 issued Mar. 22, 2011, and is a continuation-in-part application of U.S. patent application Ser. No. 12/014,340 filed on Jan. 15, 2008, now U.S. Pat. No. 7,905,904 issued Mar. 15, 2011, and is a continuation-in-part application of U.S. patent application Ser. No. 11/935,681 filed on Nov. 6, 2007, now U.S. Pat. No. 7,905,903 issued Mar. 15, 2011, and is a continuation-in-part application of 11/869,440 filed on Oct. 9, 2007, now U.S. Pat. No. 7,857,830 issued Dec. 28, 2010, and is a continuation-in-part application of 11/784,821 filed on Apr. 10, 2007, and is a continuation-in-part application of 11/347,661 filed on Feb. 3, 2006, now U.S. Pat. No. 7,749,250 issued Jul. 6, 2010, and is a continuation-in-part application of 11/347,662 filed on Feb. 3, 2006 now abandoned. This application is also a continuation-in-part of U.S. patent application Ser. No. 12/196,405 filed on Aug. 22, 2008 now U.S. Pat. No. 8,128,658, U.S. patent application Ser. No. 12/196,407, filed on Aug. 22, 2008 now U.S. Pat. No. 8,137,382, and U.S. patent application Ser. No. 12/196,410, filed on Aug. 22, 2008 now U.S. Pat. No. 8,118,836. The disclosure of the above applications is incorporated herein by reference.

INTRODUCTION

Trauma or disease in soft tissue, such as cartilage, ligament, or muscle can cause tears or detachment from bone or other defects that can be repaired by reattaching or securing the soft tissue to the bone. Various devices and methods are known for attaching and securing soft tissue to bone.

The present teachings provide a versatile tissue fixation method that can be used with various bone anchors or other implantable fixation members to attach soft tissue to bone or any tissue to other tissue.

SUMMARY

The present teachings provide a method for securing a strand to at least one fixation member for a surgical procedure, wherein the fixation member includes an aperture therethrough. The method includes passing a strand having first and second ends through a flexible sleeve, passing the sleeve through the aperture of the fixation member in a first direction, tensioning the strand, and moving the sleeve in a second direction different than the first direction to secure the sleeve to the fixation member without tying the strand on the fixation member.

The present teachings provide a method for securing a strand to a plurality of anchors for a surgical procedure. The method includes inserting a plurality of anchors into the bone, passing a flexible strand having first and second ends through a plurality of flexible sleeves serially coupled on the strand, passing each sleeve in a first configuration into and through an aperture of a corresponding anchor in a first direction, deforming each sleeve to a second configuration, and tying a single knot at the first and second ends of the strand.

The present teachings provide a method for securing a strand to a plurality of bone anchors for a surgical procedure. The method includes passing a flexible strand slidably through a plurality of flexible sleeves, forming a single slipknot on a portion of the strand outside all the sleeves, the slipknot the defining a closed loop, knotlessly securing each sleeve into a corresponding bone anchor, and reducing a length of the loop.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 3 is a perspective view of the connector device of FIG. 1, shown in engagement with a representative aperture;

FIG. 3A is a perspective view of the connector device of FIG. 1C, shown in engagement with a representative aperture;

FIG. 9 is an exemplary method of using a series of interconnected connector devices for securing soft tissues to bone.

DESCRIPTION OF VARIOUS ASPECTS

The following description is merely exemplary in nature and is in no way intended to limit the scope of the present teachings, applications, or uses. The present teachings can be used for various orthopedic applications including coupling bone to bone, bone to soft tissue, soft tissue repair, and generally attaching soft tissue to bone, or attaching suture or other anchors to bone, or any other tissue repair procedure. The present teachings can also be used for repairing any fibrous tissue, such as muscle, ligament or tendon in an arthroscopic or other open procedure, including rotator cuff reconstruction, acromioclavicular (AC) reconstruction, anterior cruciate ligament reconstruction (ACL) and generally for fastening tendons, grafts, or strands to fibrous tissue and bone. Additionally, the present teachings can be used for repairing tissue in cardiological, laparoscopic, urological, plastic, blood vessels, annulus of spine or other procedures.

Figure 1:
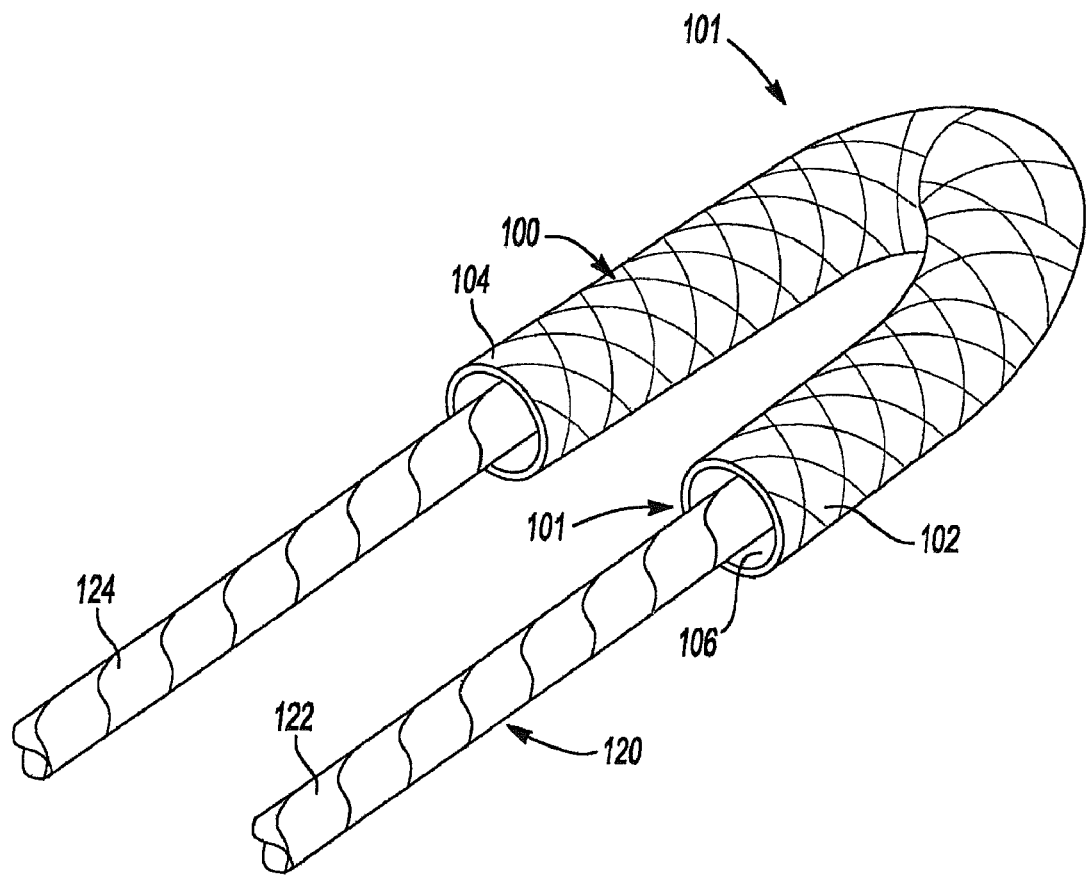
FIG. 1 is a perspective view of a connector device according to the present teachings.

Referring to FIG. 1, an exemplary connector device 101 that can be used for attaching soft tissue to bone is illustrated. The connector device 101 can include a flexible tubular sleeve or tube 100 having an inner bore 106 that extends between first and second open ends 102, 104. The sleeve 100 can be made of resorbable or non-resorbable materials, including braided suture, sponges and sponge-like, perforated materials, woven/braided from biocompatible materials or fibers, such as, for example, polymer, polyester, polyethylene, cotton, silk, or other natural or synthetic materials. The sleeve 100 can be made of suture material braided from thin filaments into a form that does not include a core filament. The sleeve 100 can have a generally flaccid shape that can be manipulated in different configurations like a piece of string or shoelace, for example. Accordingly, the sleeve 100 can be bent, folded or otherwise manipulated or deformed into various configurations, such as a bent or U-shape configuration shown in FIGS. 1, 1A and 1B, or a substantially straight configuration shown in FIG. 4, or a deformed or bunched-up, puckered configuration, such as the ball-like configuration shown in FIG. 3, or the bell-like shaped shown in FIG. 3A, as discussed below.

Figure 1A:
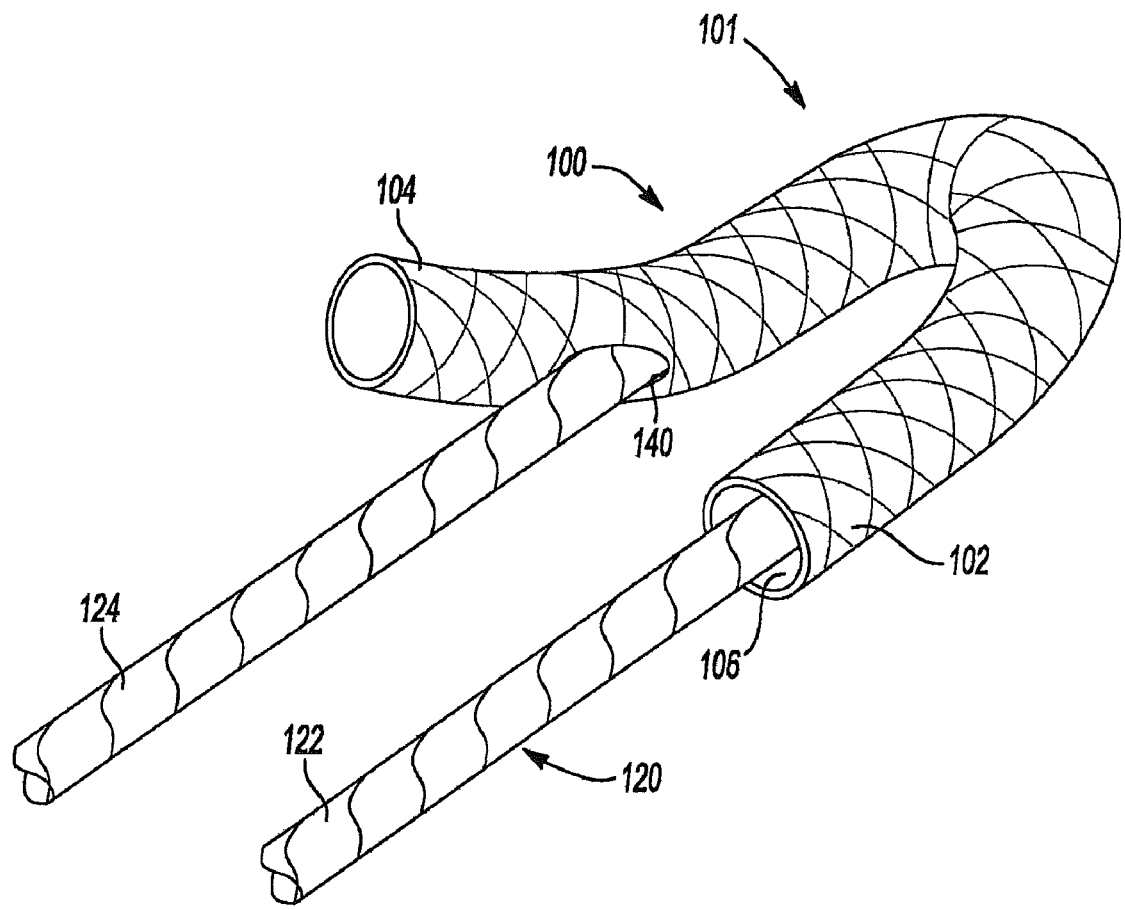
FIG. 1A is a perspective view of a connector device according to the present teachings.
Figure 1B:
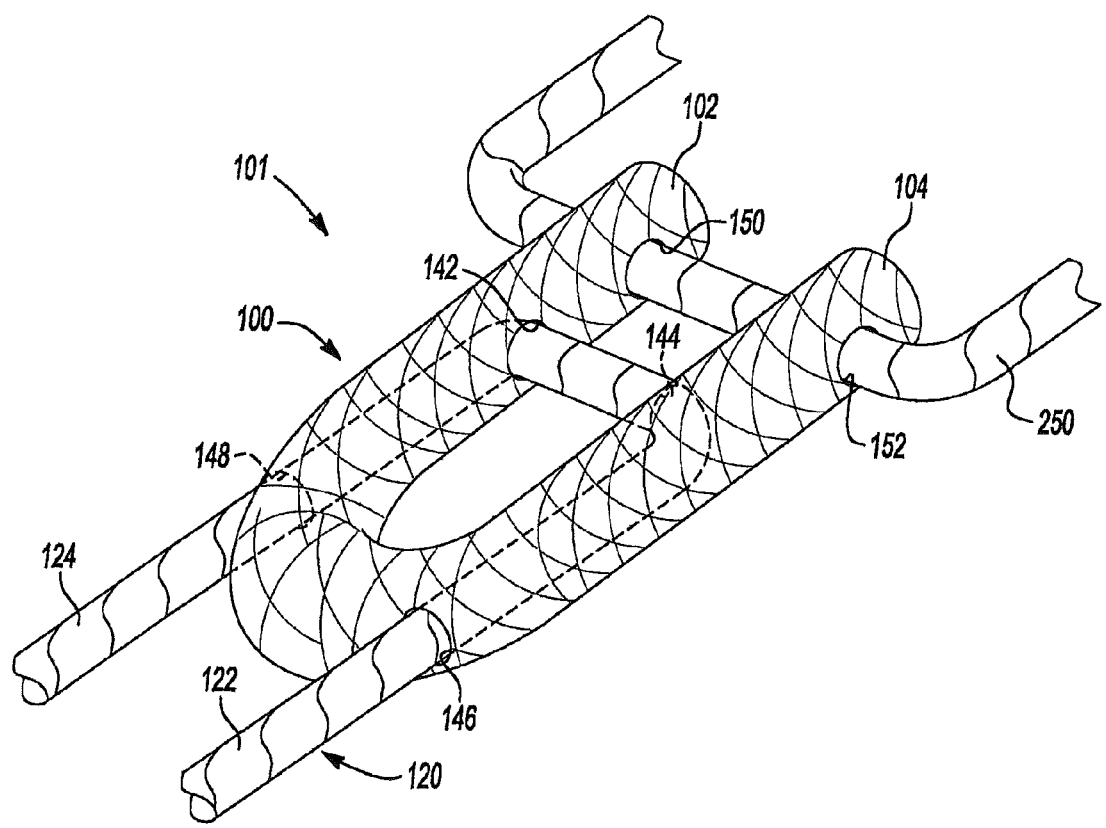
FIG. 1B is a perspective view of another connector device according to the present teachings.
Figure 1C:
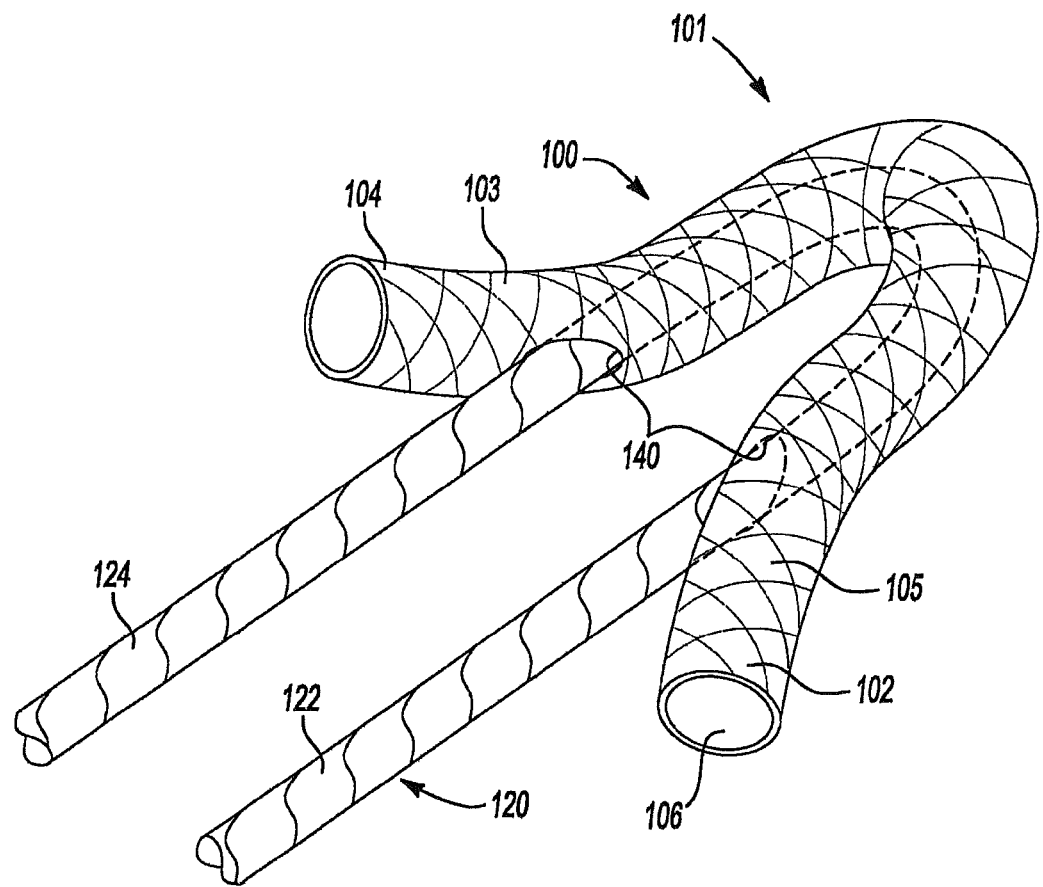
FIG. 1C is a perspective view of another connector device according to the present teachings.

Referring to FIGS. 1, 1A, 1B, and 1C the connector device 101 can also include an elongated flexible strand 120 having first and second ends 122, 124. The strand 120 can pass axially through the bore 106 of the sleeve 100, such that the first and second strand ends 122, 124 exit the corresponding first and second ends 102, 104 of the sleeve 100, as illustrated in FIG. 1. In one aspect, the strand 120 can exit the bore 106 through at least one opening 140 of the sleeve 100 intermediate the first and second ends 102, 104 of the sleeve, as shown in FIG. 1A. In another aspect, the strand 120 can exit the bore 106 through two openings 140 of the sleeve 100 intermediate the first and second ends 102, 104 of the sleeve 100, as shown in FIG. 1C. First and second end portions or sleeve legs 103, 105, are defined between each end 104, 102 and the corresponding opening 140. In another aspect, the strand 120 can pass through openings 142, 144, 146, 148, such that an intermediate portion of the strand 120 is outside the bore 106, as shown in FIG. 1B.

The strand 120 can also be made of materials similar to the sleeve 100, such as braided filaments or fibers of biocompatible material, including natural and synthetic fibers, such as cotton, silk, polymer, polyester, polyethylene, thin wire, suture, and other materials. The strand 120 can also be in the form of a flat tubular suture or a braided suture with or without a core. The connector device 101 with the sleeve 100 and strand 120 are implantable in soft tissue or bone.

Figures 2, 2A:
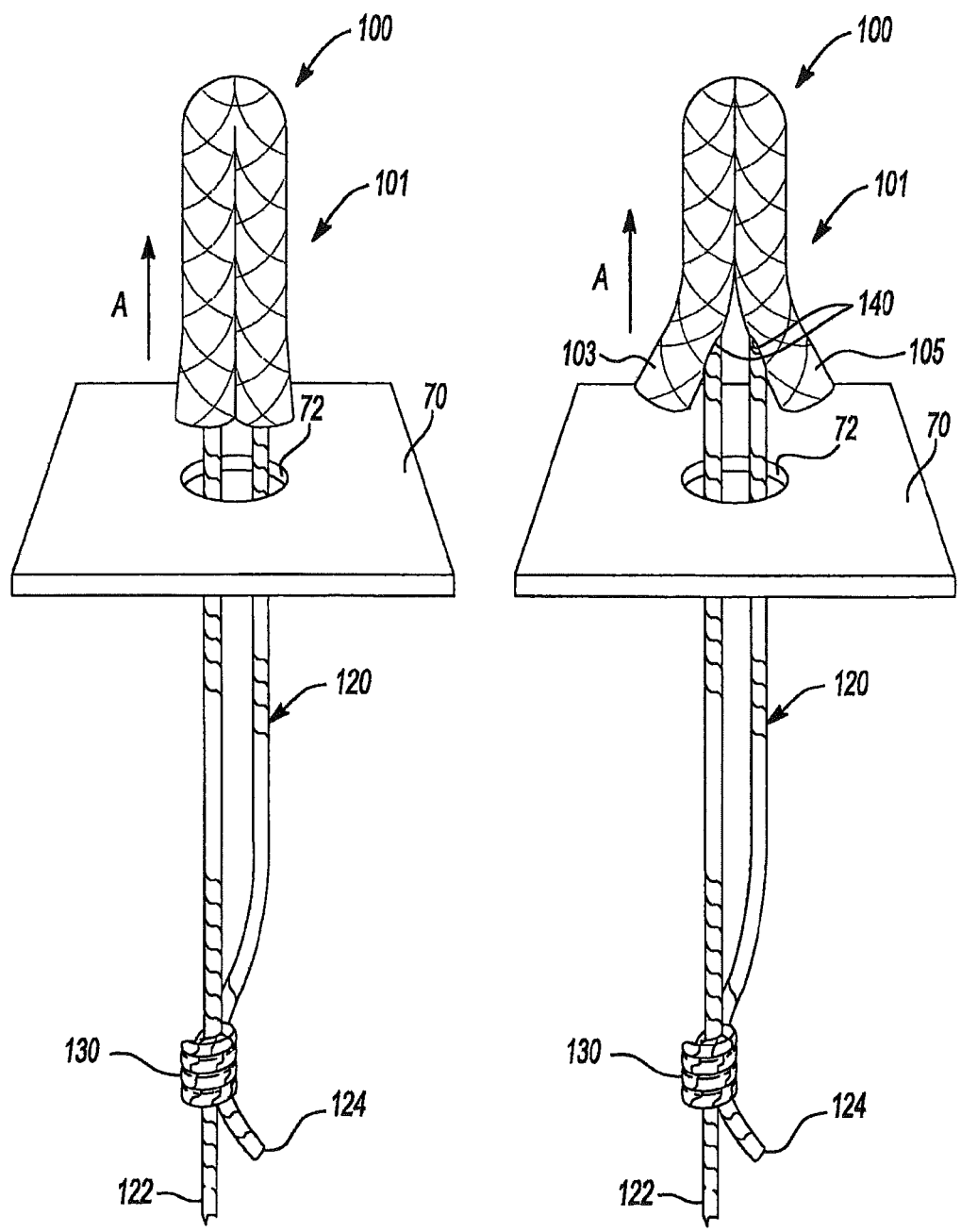
FIG. 2 is a perspective view of the connector device of FIG. 1, shown prior to engagement with a representative aperture.
FIG. 2A is a perspective view of the connector device of FIG. 1C, shown prior to engagement with a representative aperture.

Referring to FIGS. 1-3A, a general procedure for using the connector device 101 is illustrated. The sleeve 100 with the strand 120 therethrough can be folded and pushed through on orifice 72 or other aperture defined through a support 70 in the direction of arrow "A", as shown in FIGS. 2 and 2A. The strand ends of 122, 124 can be connected with a knot 130, such as slipknot, forming a strand loop 128 passing through the bore 106 of the sleeve 100.

Referring to FIGS. 2 and 3, pulling on one of the strand ends 122, 124, shortens the length of the strand loop 128 and the tension causes the sleeve 100 to change configuration, bunching up from a folded and/or flaccid configuration to a bunched-up, ball-like configuration that cannot pass through the orifice 72, such that the strand 120 can be secured on the support 70. In this configuration, the strand ends 122, 124 and the sleeve 100 remain on opposite sides of the orifice 72.

Similarly, and referring to FIGS. 2A and 3A, pulling on one of the strand ends 122, 124, shortens the length of the strand loop 128 and the tension causes the sleeve 100 to change configuration, bunching up from a folded and/or flaccid configuration to a bunched-up bell-like shape with the legs 103, 105 extended outward and pressed against the support 70. In this configuration, the sleeve 100 cannot pass through the orifice 72 in the direction of the arrow A'. The strand ends 122, 124 and the sleeve 100 remain on opposite sides of the orifice 72, and the legs 103, 105 provide additional resistance for securing the strand 120 to the support 70.

The orifice 72 can be of any shape, including any regular or irregular closed curves or polygons, or combination thereof, including circular elliptical, oval, triangular, tetragonal, hexagonal, lobed, or other shapes. The shape and size of the orifice 72 is such that the sleeve 100 in its bent shape deforms sufficiently to slide through the orifice 72 when introduced along one direction A. Once the sleeve 100 passes through and out of the orifice 72 and returns to its undeformed flaccid configuration, the sleeve 100 will bunch up against the orifice 72 when directed or pulled in the opposite direction A', as the ends 102, 104 of the sleeve 100, or the sleeve legs 103, 105, and/or deformed shape are caught against the support 70. It is noted that the strand 120 can still slide relative to the sleeve 100 and the orifice 72, therefore the orifice 72 can act effectively as an anchor eyelet.

The support 70 can be soft tissue, bone, implant, anchor or other threaded or unthreaded implantable fixation member such as those illustrated in FIGS. 5-8 at 200. The fixation members are generically referenced with numeral 200 or specifically with reference numerals 200a-200d. The connector device 101 and the fixation member 200 can form an implantable fixation assembly that can be used for securing soft tissue to bone, as further discussed below in connection with FIG. 9.

It will be appreciated that the connector device 101 can be used as a versatile suture lock that is easy to use, avoids knot-tying, and saves time during the surgical procedure. Further, as the flexible strand 120 is held against the support 70, the flexible strand 120 is prevented from pulling through without being knot-tied to the support 70. It is estimated that the flexible strand 120 can withstand a pulling force greater than that in a knot tied in the same-sized strand.

Any of the connector devices 101 illustrated in FIGS. 1, 1A, 1B, 1C, or combinations thereof, can be used with a fixation member 200 for fastening any type of ligaments, grafts or sutures, and can be used, for example, for rotator cuff repair for the shoulder, for acromioclavicular (AC) joint reconstruction, for tibial graft fixation, for ACL reconstruction, and generally for fastening tendons or grafts and sutures to tissue, including soft tissue and bone. In many of such shoulder repair procedures, a tendon is secured to the bone with many suture anchors requiring repeated knot-tying. Such knot-tying is cumbersome and time consuming during an arthroscopic procedure, as it is generally performed through an insertion cannula that is used to deliver the suture anchor. As discussed below, the connector device 101 illustrated in FIGS. 4 and 9 can be used to secure multiple suture anchors or other fixation members 200 without individual knots for each fixation member 200, and with only one final knot 130 for the entire series of fixation members 200 outside the cannula. Moreover, the knot 130 that forms the single loop 128 of the flexible strand 120 can be pre-tied.

Figure 4:
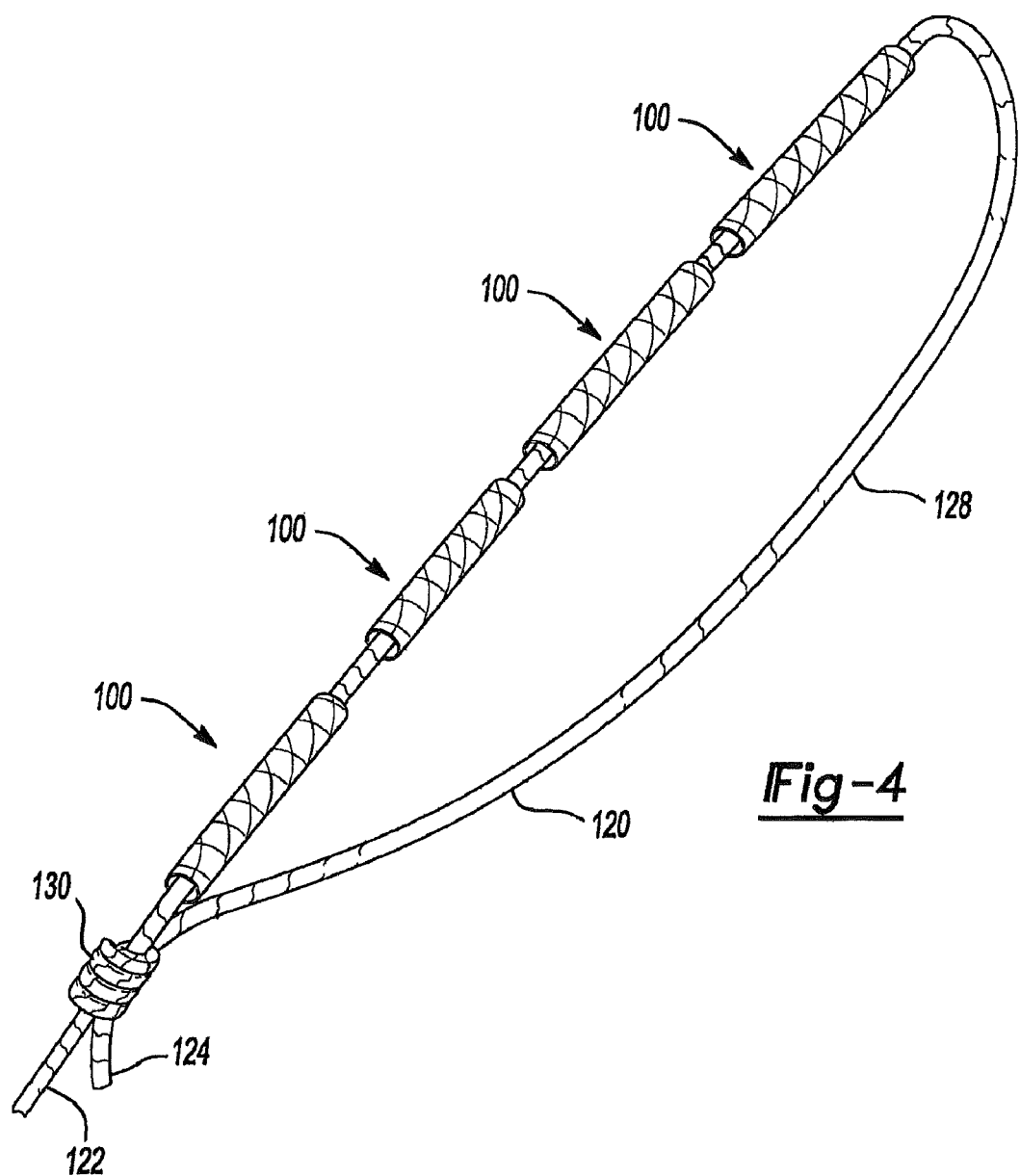
FIG. 4 is a perspective view of a series of interconnected connector devices according to the present teachings.
Figures 5, 6:
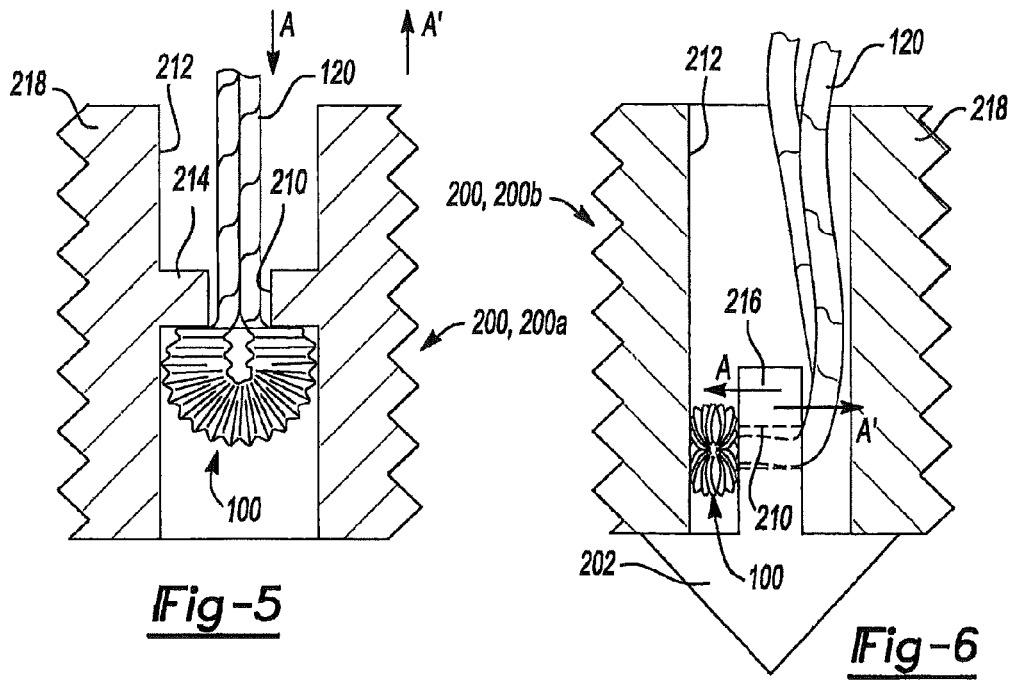
FIG. 5 is a side view of the connector device of FIG. 1, shown with a first anchor.
FIG. 6 is a side view of the connector device of FIG. 1, shown with a second anchor.

Referring to FIG. 5, the fixation member 200 can be in the form of an externally threaded open-ended tubular member 200a and can include a body 218 having an open-ended longitudinal bore 212 interrupted by a cross-wall 214. The wall 214 defines a through-slot or other aperture 210 substantially coaxial with the bore 212. The sleeve 100 can pass through the aperture 210 in a folded configuration in the direction of arrow A, while the strand ends 122, 124 of the strand 120 remaining outside the fixation member 200. The sleeve 100 can be held against the wall 214 in a bunched-up (ball or bell-like) configuration when pulled by the strand 120 in the direction A'. In the same manner, a plurality of sleeves 100 strung together in a single loop 128 of a single strand 120, as shown in FIG. 4, can be secured to a corresponding plurality of fixation members 200, without requiring individual knots, as shown in FIG. 9 and discussed below. Using a plurality of sleeves 100 in a single loop 128 allows a fast and efficient procedure of creating a suture mat for attaching soft tissue 80 to bone 84 in multiple locations without having to tie knots arthroscopically through a cannula for each individual fixation member 200.

Referring to FIG. 6, the fixation member 200 can be an implant in the form of a tubular anchor 200b having a body 218 and include a longitudinal bore 212 closed at one end with a pointed anchoring tip 202. The anchoring tip 202 can be integrally or removably coupled to the body 218. The anchoring tip 202 can include a longitudinal extension 216 received in the bore 212. The extension 216 can define an aperture 210 substantially parallel with the bore 212. The sleeve 100 can be passed through the aperture 210 in the direction of arrow A, such that the strand 120 passes through the aperture 210, through the bore 212 and exits the fixation member 200. The sleeve 100 can be held between a wall of the bore 212 and the extension 216 in a bunched-up (ball or bell-like) configuration after the strand 120 is pulled away from the fixation member 200 in another direction, such as the direction of arrow A'. It should be appreciated that the directions A and A' need not be opposite. Pulling in any direction A' that will cause the strand 120 to tension can suffice. Although FIGS. 5 and 6 illustrate examples of an aperture 210 that is respectively coaxially or perpendicularly oriented relative to the bore 212 of the fixation member 200, it will be appreciated that the aperture 210 is not limited to these orientations. The fixation member 200b can also be used in a single loop 128 with multiple similar or different fixation members 200 for attaching soft tissue 80 to bone 84 in multiple locations, as illustrated in FIG. 9.

Figures 7, 8:
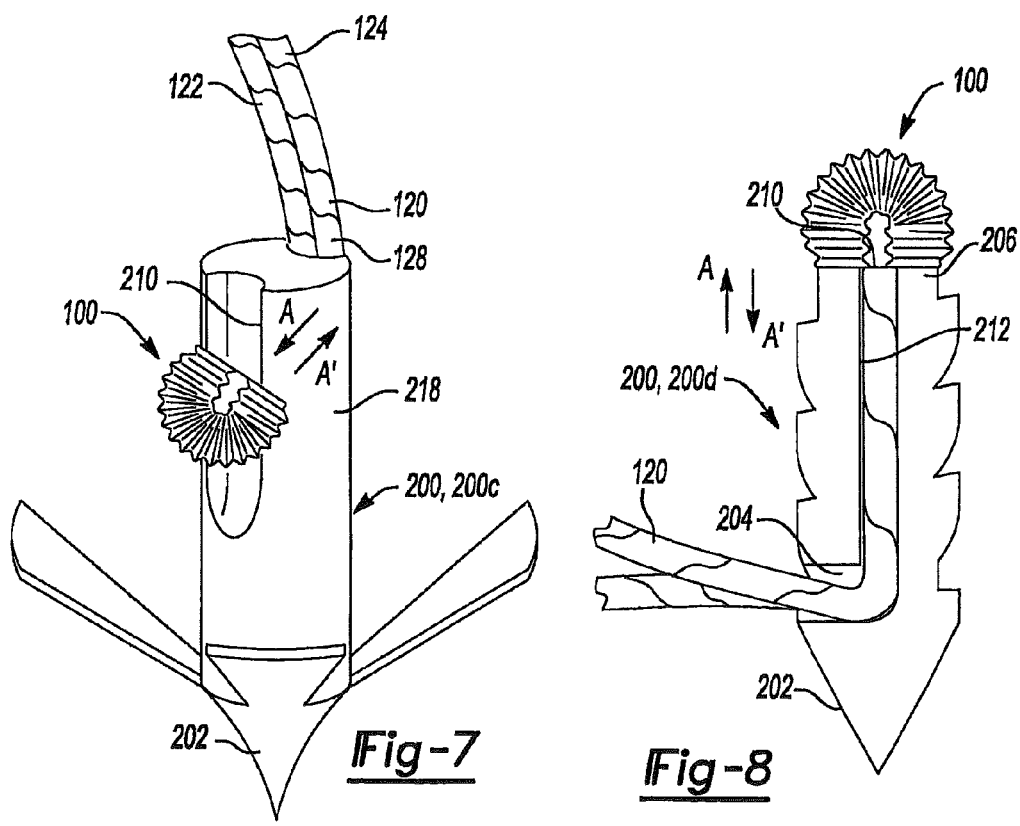
FIG. 7 is a side view of the connector device of FIG. 1, shown with a third anchor.
FIG. 8 is a side view of the connector device of FIG. 1, shown with a fourth anchor.
Figure 10A:
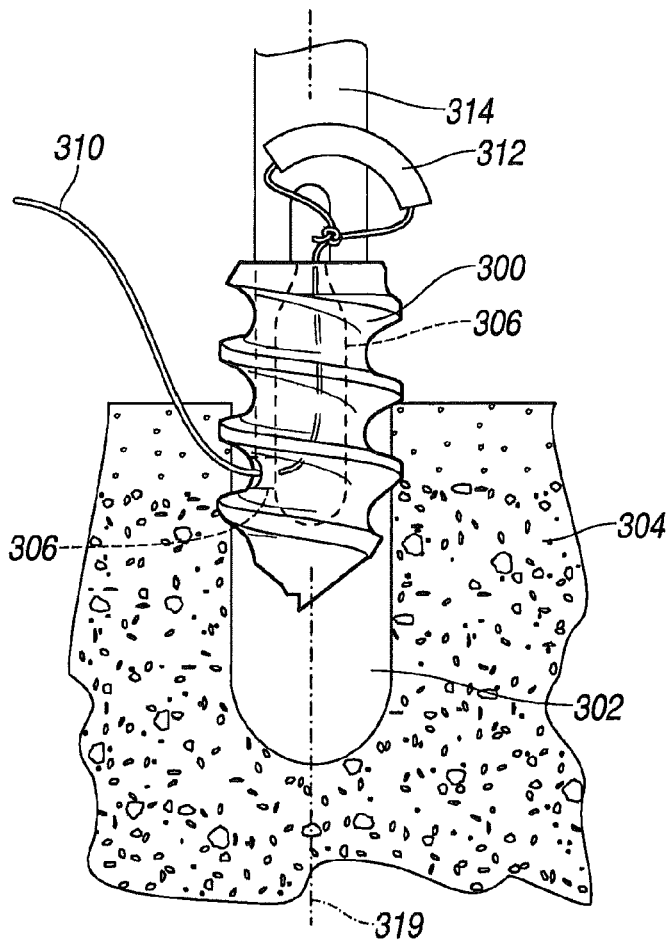
FIGS. 10A-15 represent various suture constructions coupled to a hollow fixation element.
Figure 10B:
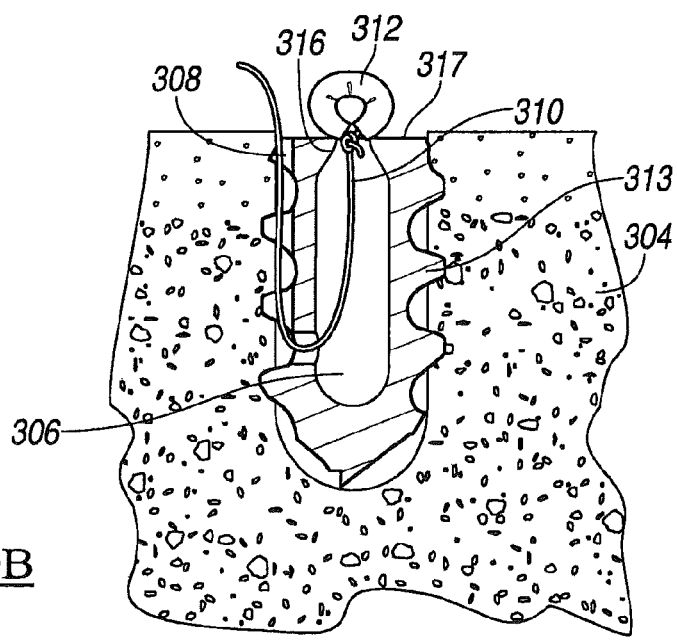
Figure 11A:
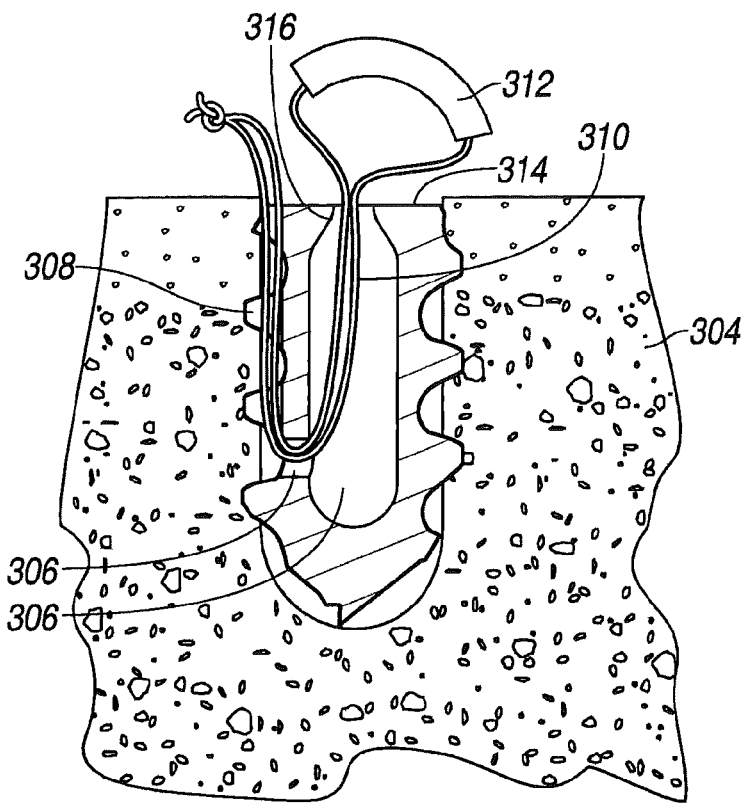
Figure 11B:
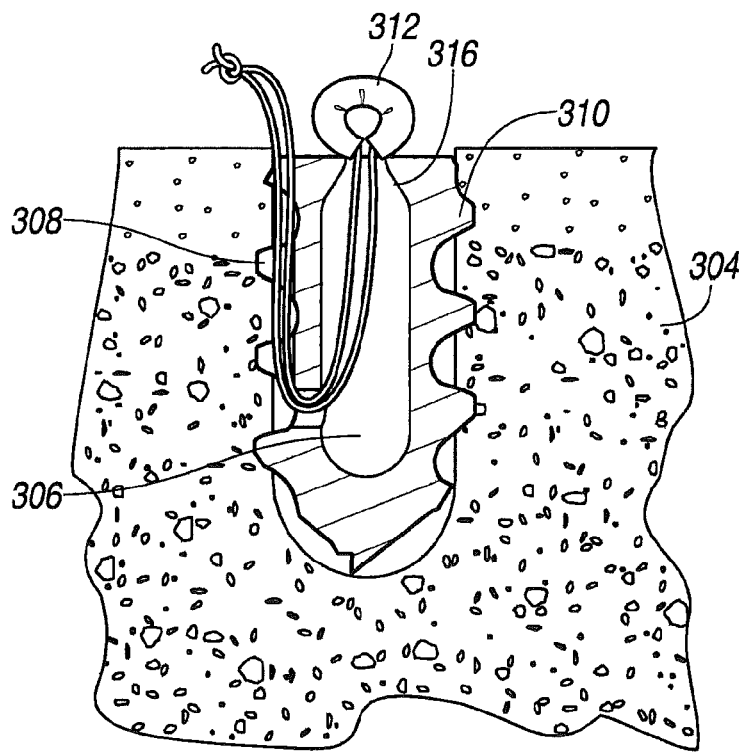
Figure 12A:
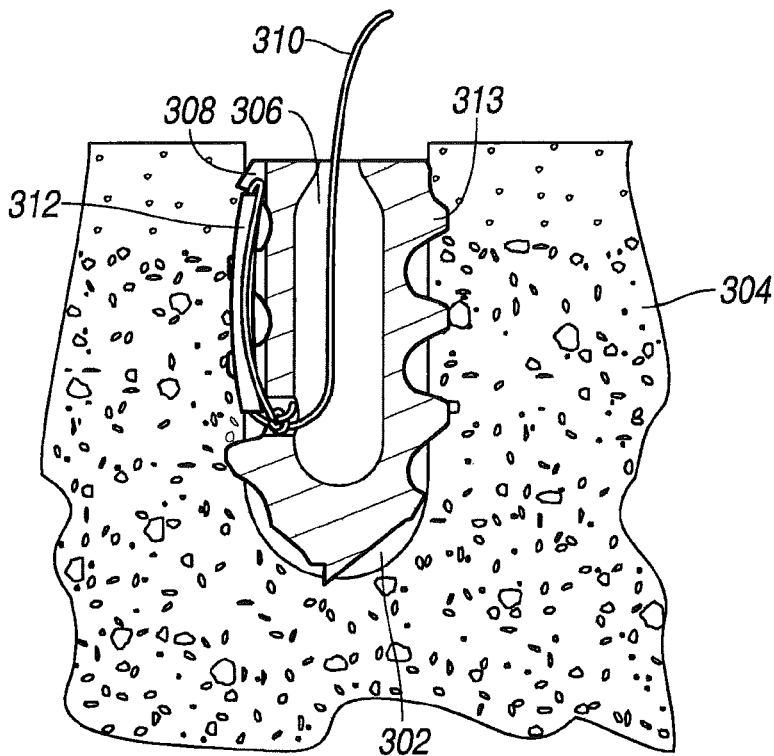
Figure 12B:
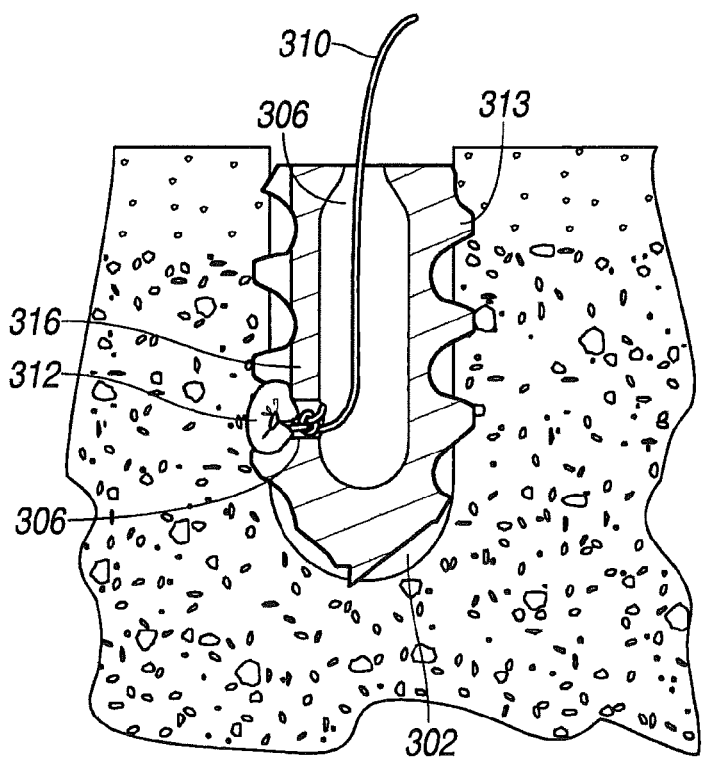
Figure 13:
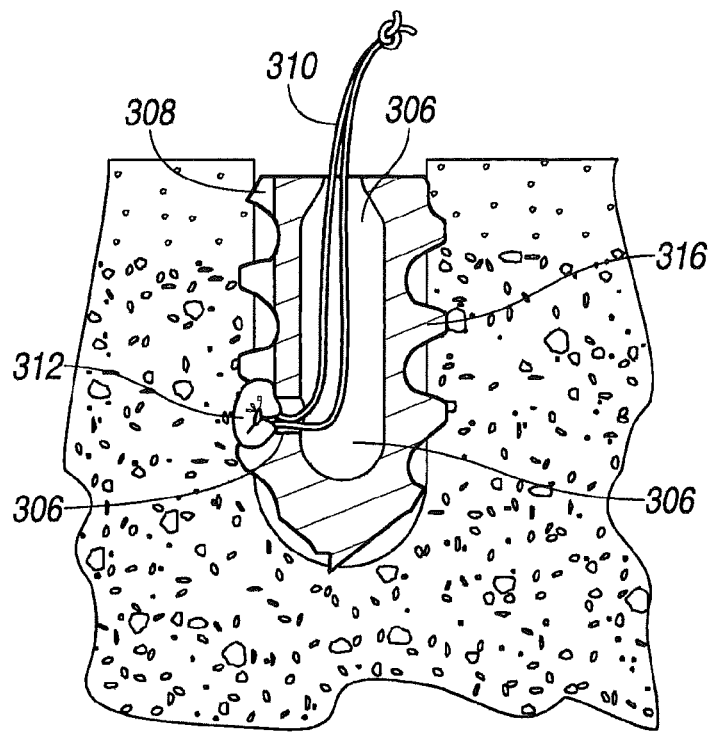

Referring to FIG. 7, the fixation member 200 can be an implant in the form of harpoon-type anchor 200c having a pointed anchoring tip 202. The fixation member 200 can include a central body 218 defining an aperture 210. The sleeve 100 can be passed through the aperture 210 in the direction of arrow A. The strand 120 can form a loop 128 passing through the aperture 210 in the direction of arrow A. The strand ends 122, 124 can be pulled away from the fixation member 200 in the direction of arrow A', such that the sleeve 100 is held against the body 218 in a bunched-up (ball or bell-like) configuration. The fixation member 200c can also be used in a single loop 128 with multiple similar or different fixation members 200 for attaching soft tissue 80 to bone 84 in multiple locations, as illustrated in FIG. 9.

Referring to FIG. 8, the fixation member 200 can be an implant in the form of an externally threaded suture anchor 200d having a body 218 with an anchoring tip 202 and including a longitudinal bore 212 extending from a proximal end 206 to a distal eyelet 204. The sleeve 100 can be passed through the eyelet 204, the bore 212 and the aperture 210 defined at proximal end 206 of the bore 212 in the direction of arrow A. The strand 120 can form a loop 128 passing through the bore 212 and exiting the eyelet 204. The strand ends 122, 124 can be pulled away from the fixation member 200 in the direction of arrow A', such that the sleeve 200 can be secured against the proximal end 206 in a bunched-up (ball or bell-like) configuration. The fixation member 200d can also be used in a single loop 128 with multiple similar or different fixation members 200 for attaching soft tissue 80 to bone 84 in multiple locations, as illustrated in FIG. 9.

The connector device 101 can be pushed through the aperture in the fixation member 200 using an inserter, such as the inserter 300 shown in FIG. 9 and the inserter described and shown in FIGS. 8A-9B and 13-15 of the cross-referenced patent application Ser. No. 11/347,661 filed on Feb. 3, 2006, although other inserters can also be used. The sleeves 100 of the connector device 101 can be coupled to corresponding fixation members 200, either before or after the fixation members 200 are secured in the bone 84.

Referring to FIGS. 4 and 9, a series of sleeves 100 can be strung along a single loop or chain 128 of the strand 120 without other knots except a single slipknot 130 coupling the strand ends 122, 1224. Each sleeve 100 can be inserted in a corresponding prepared bone bore 84 or in a corresponding fixation member 200 to attach soft tissue 80 to a bone 84. It will be appreciated that identical or different fixation members 200, such as, for example, fixation members 200a-200d, can be used for securing the corresponding sleeves 100, and one or more fixation members 200 can be omitted, such that the sleeve 100 is secured directly in a bone bore 86 without using a fixation member 200. Some exemplary options are illustrated in a single illustration in FIG. 9.

It will be appreciated that the sleeve 100 can be inserted or secured to the fixation member 200 either before or after the fixation member 200 has been implanted into the bone 84. For example, the sleeve 100 can be secured to the fixation member 200 prior to bone implantation, either manually or by using an inserter, such as the inserter 300 that includes a tip 302 and a hook 304 in which the sleeve can be supported in a folded, U-shape configuration with the strand 120 therethrough. Alternatively, and as illustrated in FIG. 9 in connection with the fixation member 200a, the fixation member 200a can first be implanted into bone 84. The tip 302 of the inserter 300 with the sleeve 100 thereon can be pushed through the aperture 210 of the fixation member 200a in the direction of arrow A.

Referring to FIG. 9 and in connection with the exemplary fixation member 200c, another method of securing the sleeve 100 to the fixation member 200c, after the fixation member 200c is implanted, is illustrated. Specifically, an auxiliary flexible member or string 250 in the form of a monofilament made of polyethylene, polyester, silk, or other biocompatible fiber or thin string-like material can be looped around the sleeve 100 and passed through the aperture 210 of the fixation member 200c. Pulling the auxiliary member 250 in the direction of arrow "B" causes the sleeve 100 and portion of the strand 120 to pass through the aperture 210 in a folded configuration. The auxiliary member 250 can be then pulled out and completely removed from the sleeve 100 and fixation member 200c. The sleeve 100 can be secured to the fixation member 200c in a bunched-up (ball or bell-like) configuration by pulling on the ends 122, 124 of the strand loop 128 to shorten the loop 128, as described above. In another aspect, the auxiliary flexible member 250 can be looped through openings 150, 152 of the sleeve 100, as shown in FIG. 1B.

With continued reference to FIG. 9, fixation member 200d is shown implanted in bone bore 86 with the sleeve 100 shown in a bunched-up (ball or bell-like) configuration. Another fixation member 200d' is illustrated before implantation into the bone bore 86. The fixation member 200d' can be coupled to a cannulated or other fixation-member inserter 270 for insertion through an incision or other opening 82 in soft tissue 80 and into a bone bore 86. The opening 82 can be pre-formed with another surgical instrument or by the pointed tip 202 of the fixation member 200d' as it is pushed through the soft tissue 80. Similarly, the bone bore 86 can be pre-formed, or created by the threaded fixation member 200d' as it is threadably inserted into the bone 84. An auxiliary member 250 can be used to manipulate the sleeve 100 and secure the sleeve 100 into the fixation member 200d', as described above in connection with fixation member 200c. The auxiliary member 250 can be looped around the sleeve 100 and passed through the eyelet 204 into the bore 212 and out of the aperture 210 at the proximal end 206. The sleeve 100 can be pulled through the eyelet 204, the bore 212 and aperture 210 by pulling the auxiliary member 250 in the direction of the arrow B either before or after implantation of the fixation member 200d' into the bone 84.

After all the sleeves 100 have been secured to the corresponding fixation members 200, the single loop 128 is tightened by pulling one of the strand ends 122, 124 relative to slipknot 130. In this manner, tissue to tissue attachment in multiple locations without the need of individual knots for each location is conveniently performed, thus avoiding the need of tying individual knots through cannulas for each fixation member 200. The procedure can be used for any tissue to tissue attachment, including, but not limited to, various arthroscopic procedures, such as, for example, rotator cuff repair, acromioclavicular reconstruction, and other procedures for which multiple anchor fixation can be beneficial. The procedure can be performed efficiently by simply passing by pulling or pushing the connector device 101 through an aperture or eyelet of the anchor or other fixation member 200 in one direction and then tensioning or pulling the strand 120 of the connector device 101 in the another direction for a knotless attachment of the strand 120 to the fixation member 200. The pull-out strength of the attachment can be a function of the strand size, but greater than using a mere strand with a knot.

Generally, and described above, the connector device 101 including one or more sleeves 100 can be to secure a strand 120, such as a suture to soft tissue 80 or bone, and to attach soft tissue to bone. Any of the connector devices 101 illustrated in FIGS. 1, 1A, 1B and 1C, can be used with or without a fixation member 200 and with or without an inserter 300 and with or without an auxiliary member 250 for manipulation the sleeve 100, although only the connector 101 of FIG. 1 is shown in the exemplary illustrations of FIGS. 4-9. Accordingly, a fixation assembly kit can be provided that includes, for example, a plurality of sleeves 100, a cartridge of continuous stand 120 or separate pieces of strand 120, a cartridge or separate pieces of auxiliary member material, one or more inserters, various fixation members 200, and one or more fixation member inserters 270. The sleeves 100 and strand 120 can be provided preloaded on one or more inserters 300.

When a fixation member 200 is used, the fixation member 200 can be provided preloaded on a fixation member inserter 270. The connector device 101 allows tissue to tissue attachment in multiple locations without the need of individual knots for each location. After multiple-location attachment is performed, the single loop 128 is tightened by pulling one of the strand ends 122, 124 relative to slipknot 130.

With general reference to FIGS. 10A-15, shown is a fastener 300 which is coupled to a bore 302 defined within a bone 304. The fastener 300 defines a suture accepting aperture 306 and a suture accepting channel 308. In this regard, the suture accepting channel 308 is defined on an exterior surface of the fastener 300 and can intersect the aperture 306. Coupled to the fastener 300 is a suture construction 310 as previously described.

The fastener 300 has an exterior surface having a bone engaging flange 313. This bone engaging flange 313 can be a helical thread which circumscribes a central axis 319 defining the fastener 300. The suture construction 310 is fed in a first direction through the suture accepting aperture 306. Optionally, defined adjacent a suture bearing surface 317 of the fastener 300, is a portion of the suture accepting aperture having a restricted diameter 316. As will be described further below, the restricted diameter 316 and bearing surface 317 are configured to engage first and second ends of the flexible sleeve 312 to facilitate the collapsing or change in cross-section of the flexible sleeve 312 when the flexible sleeve 312 is pulled in a second direction. This allows the locking engagement of the suture construction 310 to the fastener 300.

Shown in FIGS. 10A-11B are fasteners 300 engaged within the bore 302 in bone 304. Shown are sutures 310 fed through the suture accepting aperture 306 and then through the channel 308 which is defined in the exterior surface of the fastener 300 and/or within the bone engaging flange 313. As shown in FIGS. 12A-15, the flexible sleeve can be positioned within the suture accepting channel 308 prior to the insertion of the fastener 300 within the bore 302 defined in the bone 304. Upon application of tension to the single or multiple suture strands 310, the suture can be translated in the second direction through the aperture 306 having a restricted diameter 316 to cause engagement of and subsequent collapsing of the flexible sleeve 312. This collapsed sleeve 312 has a second cross-section which allows for the interference of the threads within the bore 302 defined in the bone 304, thus restricting the rotation of the fastener 300 within the bore 302. Further, the collapsing of the tube 312 allows for the fixing of the suture 310 to the fastener 300.

Figure 14:
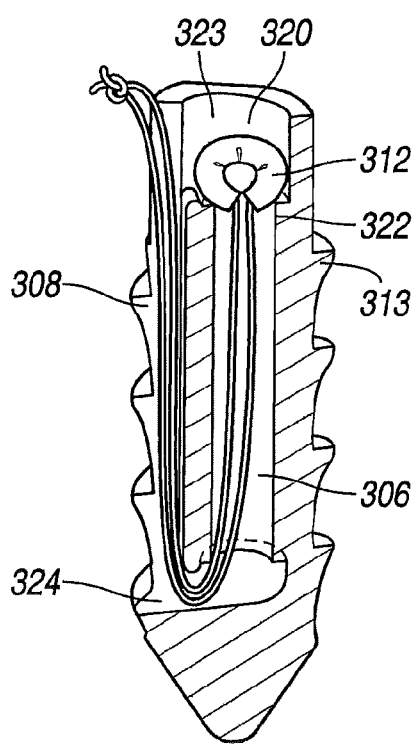
Figure 15:
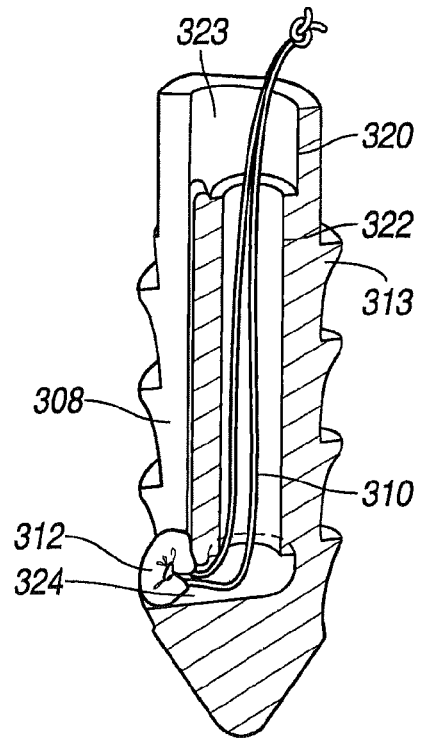
Figure 16A:
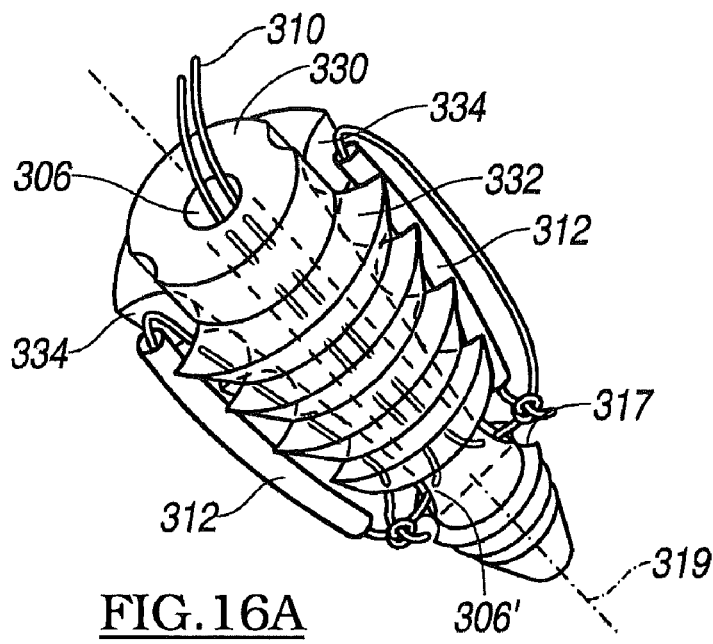
FIGS. 16A-18C represent alternate fasteners and suture constructions according to the teachings of one embodiment.
Figure 16B:
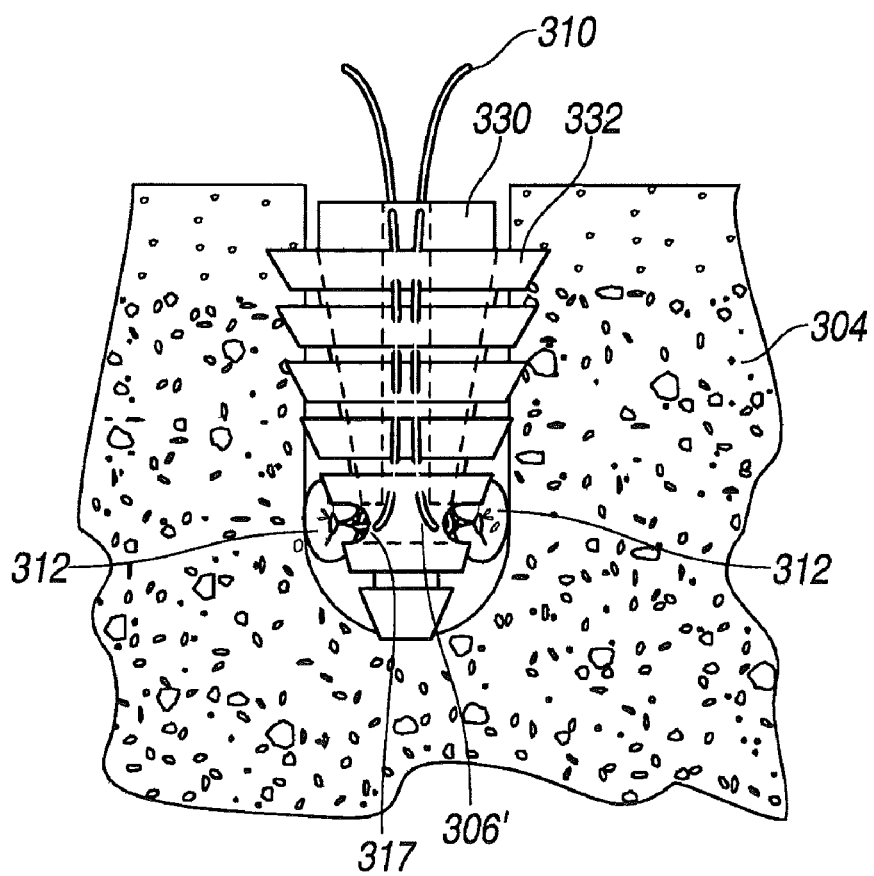
Figure 17:
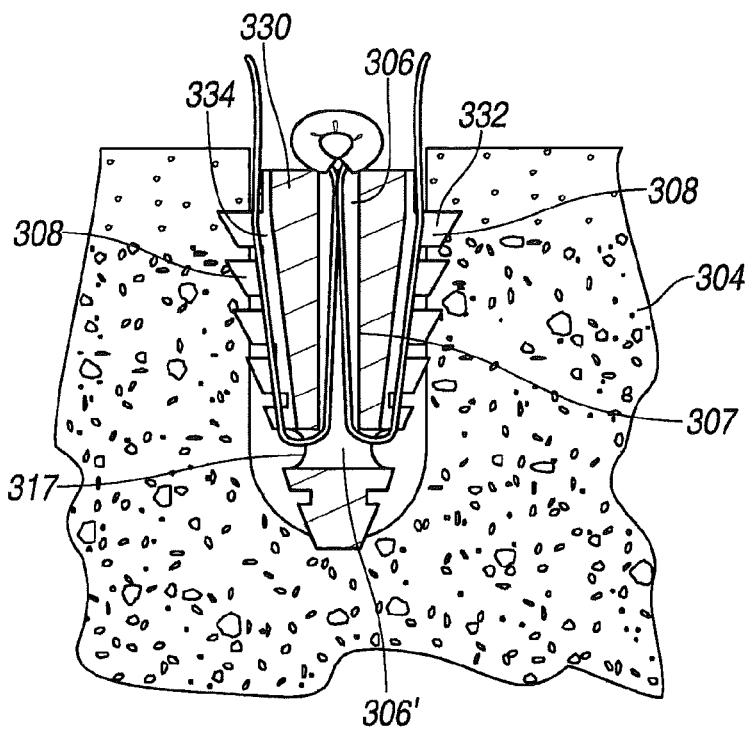
Figure 18A:
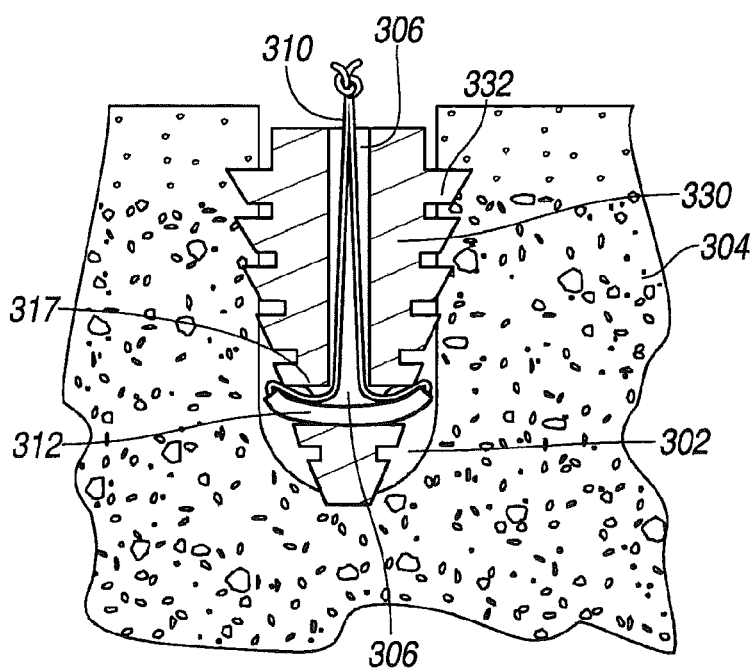
Figure 18B:
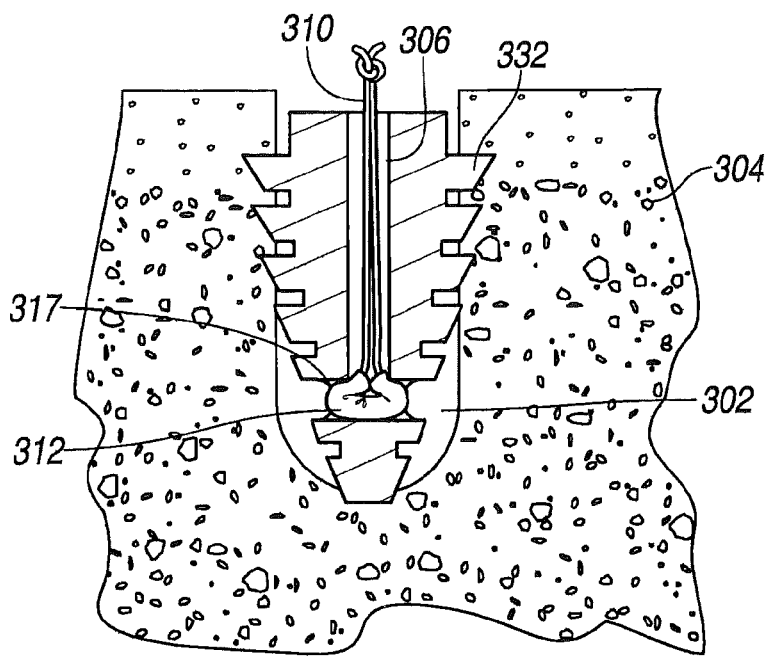
Figure 18C:
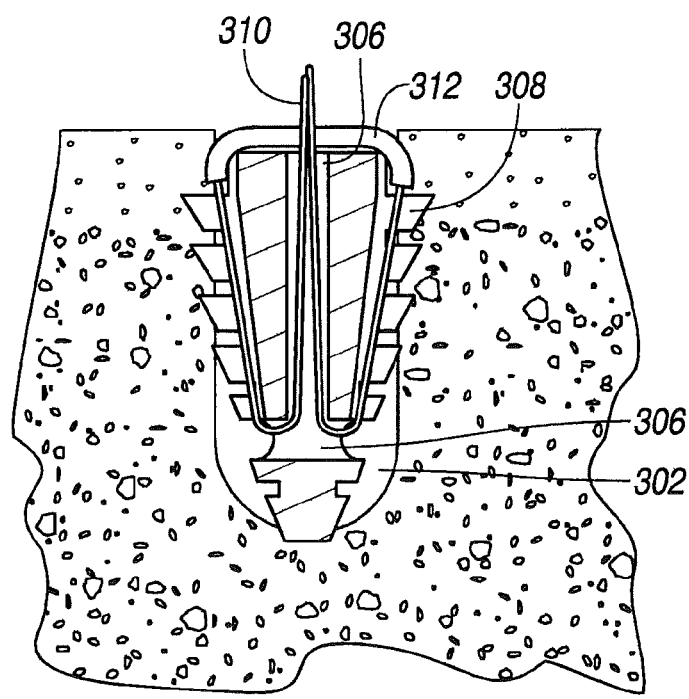

As best seen in FIGS. 14 and 15, the suture accepting aperture 306 can have various profiles. In this regard, the suture accepting aperture 306 can have a first portion having a first diameter 320 and a second portion 322 having a second diameter smaller than the first portion. This first portion 320 can define a chamber 323 which functions to accept the collapsed flexible sleeve. Additionally, the channel 308 can be sized so as to allow the collapse of the flexible sleeve 312 in a manner which would not restrict the rotation of the fastener 300 within the bore 302 defined within the bone. Drive surfaces can additionally be formed within the chamber 323.

With general reference to FIGS. 16A-18C, shown are an alternate fastener 330 which is used to couple suture 310 to a bone 304. The fastener 330 has a central suture accepting aperture 306 which is generally defined along a central axis 319 of the fastener 330. Additionally, defined generally perpendicular to the center line of the fastener is a second suture accepting aperture 306'. The fastener 330 has a plurality of bone engaging flanges 332 which are radially disposed about the central axis 319. The bone engaging flanges 332 can be formed generally perpendicular to the central axis 319.

As best seen in FIGS. 16B-18B, the fastener 330 can have a generally conical shape to facilitate the insertion of the fastener 330 within the bore 302. This conical shape can also be defined on the exterior surface of the bone engaging flanges 332. Defined within the bone engaging flanges 332 or an exterior surface of the fastener 330 can be a pair of suture or flexible sleeve accepting channels 334. Prior to insertion of the fastener 330 into the bore 302, either of the suture and/or a non-compressed flexible sleeve 312 can be positioned within the channels 334.

The fastener 330 can be liner or rotatably inserted into the bore 302. After insertion of the fastener 330 within the bore 302, tension is applied to one or more of the suture strands 310 to cause the movement of the flexible sleeve 312 in a first direction. This causes the flexible sleeve 312 to engage a bearing surface 317 of the fastener 330. The engagement of the flexible sleeve 312 with the bearing surface 317 causes the collapse of the flexible sleeve as been previously described. This functions to lock the suture 310 to fastener 330 and to increase retention forces between the fastener 330 and the bore 302.

Figure 19A:
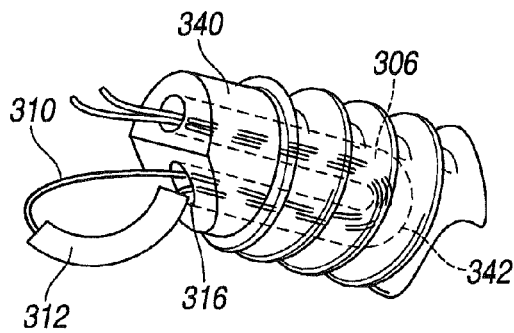
FIGS. 19A-20 represent an alternate fastener and suture construction.
Figure 19B:
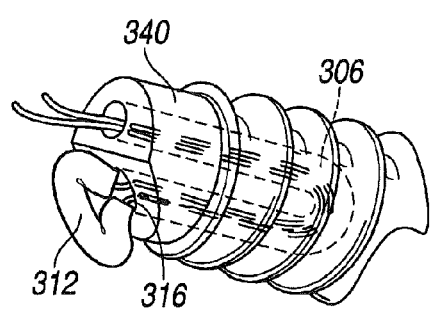
Figure 19C:
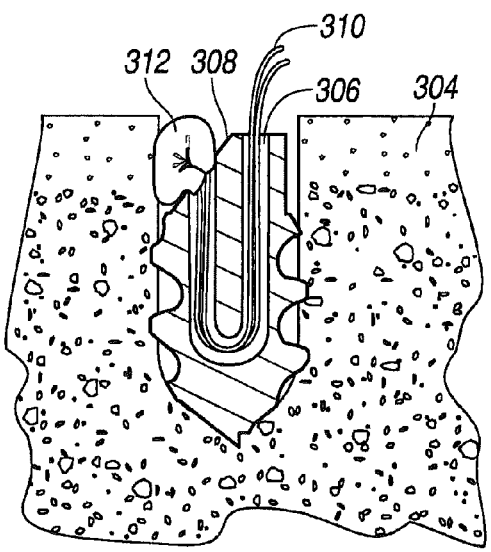
Figure 20:
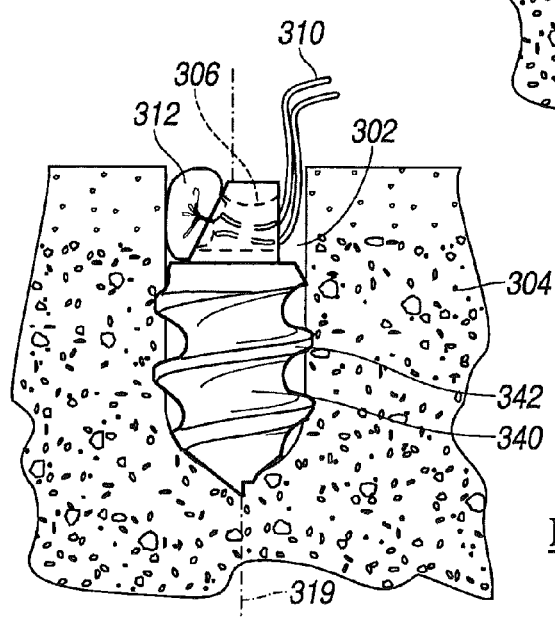
Figure 21:
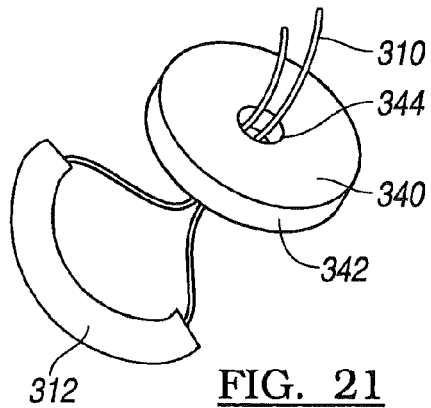
FIGS. 21-24 represent an alternate fastener and suture construction according to the present teachings.
Figure 22:
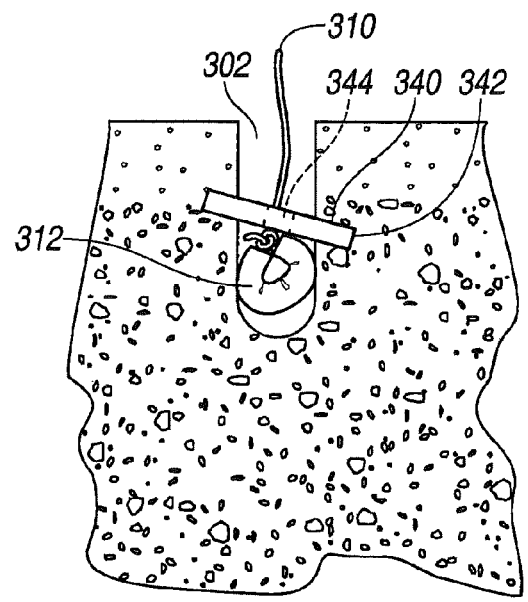
Figure 23:
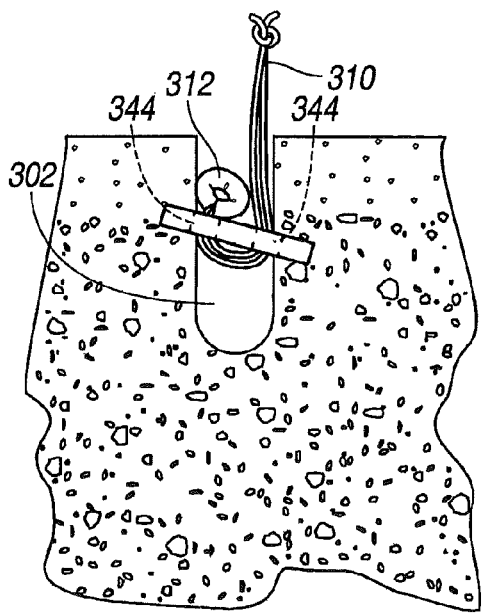
Figure 24:
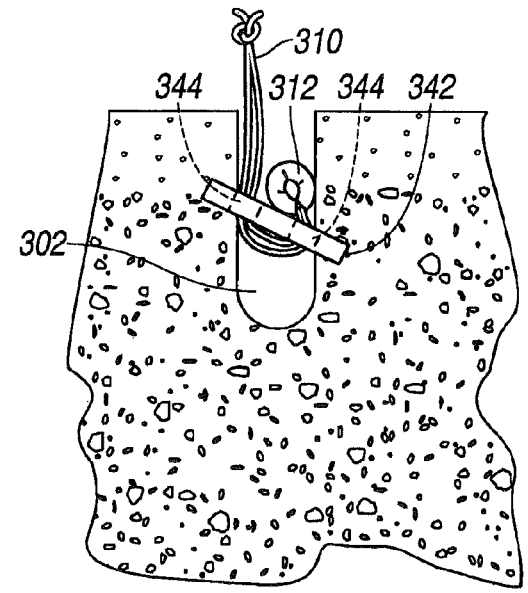

FIGS. 19A-20 represent an alternate fastener 340 coupled to a suture 310. The fastener 340 has a suture accepting bore 306 defined therein. This bore 306 can have portions which are parallel to and/or perpendicular to a central axis 319 defining the fastener body. The exterior of the fastener defines a channel or cutout 308 which functions to accept the collapsible sleeve 312 threaded onto the suture 310. This cutout 308 can be accessible through the bore 302 once the fastener 340 is inserted.

FIGS. 19C and 20 depict cross-sectional and side views of the fastener 340 inserted within a bore 302 defined within bone 304. Once tension is applied to the collapsible sleeve 312 and suture 310, the sleeve 312 is pulled into a pocket defined by the channel or cutout 308. This collapsible sleeve 312 can bear upon an interior surface of the bore 302 as well as the channel or cutout 308 to lock a suture 310 to the fastener 340, as well as aid in the fixation of construct in bone. Also shown are bone engaging flanges 342 which couple the fastener to bone 304.

As seen in FIGS. 21-24, an alternate anchor 340 is positioned within an aperture 302. The anchor 340 is rotated within the aperture 302 to engage the bone. Application of tension to an end or ends of the suture 310 can cause the anchor 340 to rotate and engage the bone. The alternate suture anchor 340 is coupled to a suture 310 and a collapsible sleeve 312. Optionally, the anchor 340 can take the form a generally flat cylinder or tube having a bone engaging surface 342 and a suture accepting bore 344 therethrough. While shown as a disk, it is envisioned the anchor 340 can have an elongated profile.

Application of tension to an end or ends of the suture construction 310 can cause the anchor 340 to rotate and engage the bone and to cause the collapse of the flexible sleeve 312. This fixably couples the suture 310 to the anchor 340 as well as the bone 304.

Figure 25A:
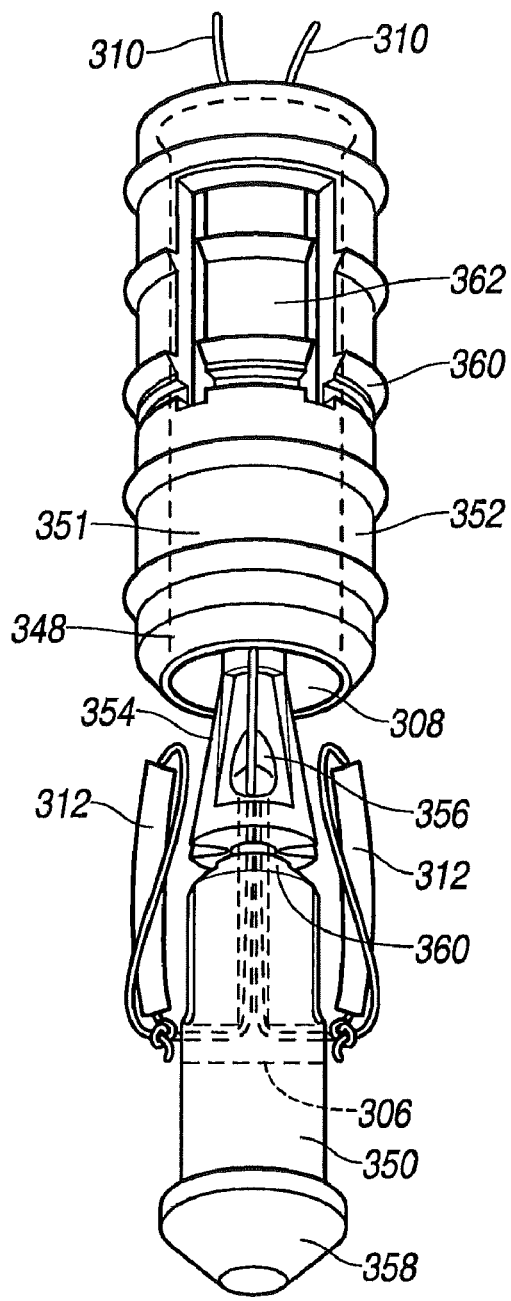
FIGS. 25A and 25B represent two-part fasteners and suture construction.
Figure 25B:
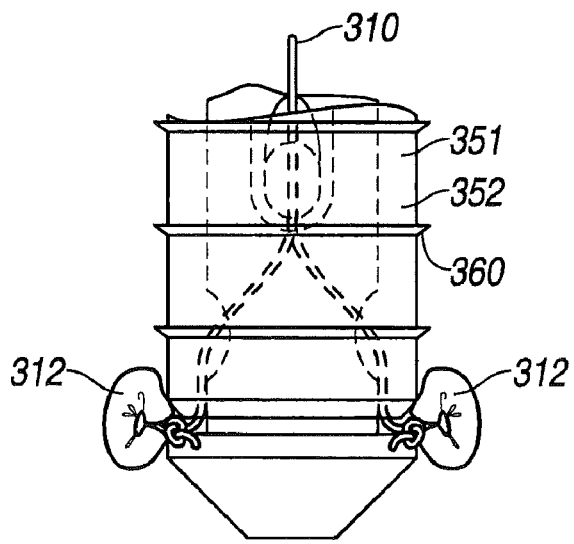

FIGS. 25A and 25B represent a fastener 348 having first and second portions 350, 352. Additionally shown is an insertion tool 354 which is used to facilitate the first and second fastener portions 350, 352 into an aperture 302 defined within a bone 304. The first portion of the fastener 348 has a head 358 which can have a generally conical shape. Additionally, the head 358 can have a bearing surface which functions, to constrain the movement of the suture construction 310 and/or the collapsible flexible tube 312.

The second fastener portion 352 has an interior portion 308 which can facilitate the acceptance of the flexible sleeve 312. Defined on an outer surface of the second portion 352 can be a plurality of bone engaging flanges 360. Optionally, the second portion can have an expandable member 362 which facilitates the engagement of the flanges 360 into the bone 304 upon the coupling of the first and second portions 350, 352. For installation, a central tool 354 has a pair of apertures with suture ends 310 threaded therethrough. The suture 310 can have a pair of flexible sleeves 312 being mounted thereon. These flexible sleeves 312 are optionally threaded through the suture accepting bore 306 defined within the first portion 350 of the two portion fastener 348.

FIG. 25B represents an assembled two component fastener 348 shown in FIG. 25A. In this regard, the first portion 350 is disposed within the central aperture 351 in the second portion fastener 352. As can be seen, the suture 310 is disposed between the first and second portions 350, 352. Application of tension to the suture 310 causes the collapse of the flexible sleeve 312 and associated locking of the suture construction 310 to the fastener 348.

Figure 26A:
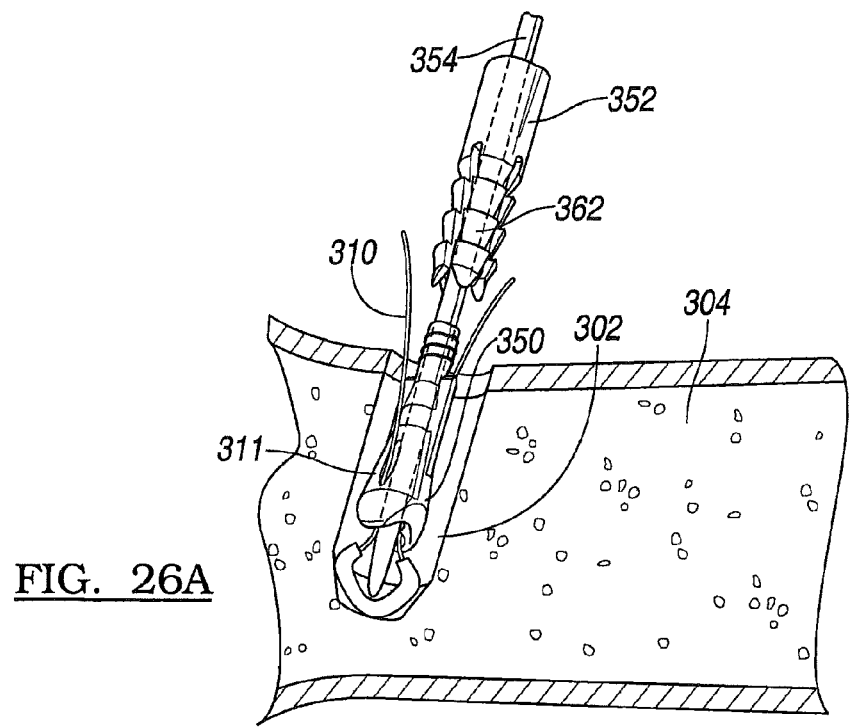
FIGS. 26A-26C represent the insertion of the fastener shown in FIGS. 25A and 25B.

With general reference to FIGS. 26A-27, shown is the insertion of a two-part fastener 348 according to the present teachings. Shown is the first portion 350 having a tapered smooth exterior surface, and a second fastener portion 352 having a plurality of movable bone engaging flanges 362. A pair of apertures 306 defined within the first fastener 350 accept the suture 310 and flexible sleeve 312.

Figure 26B:
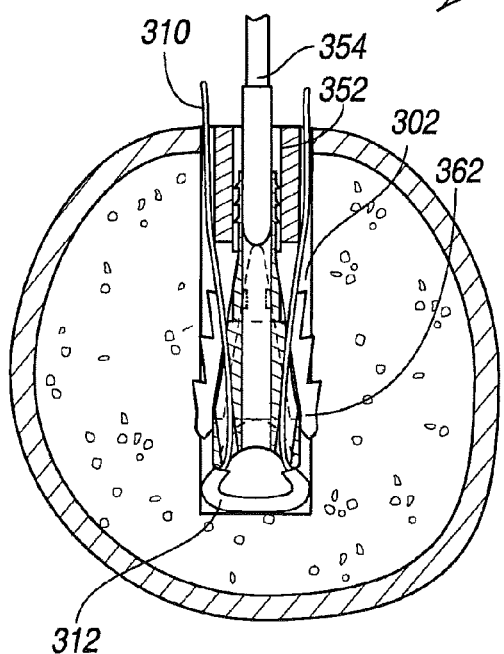
Figure 26C:
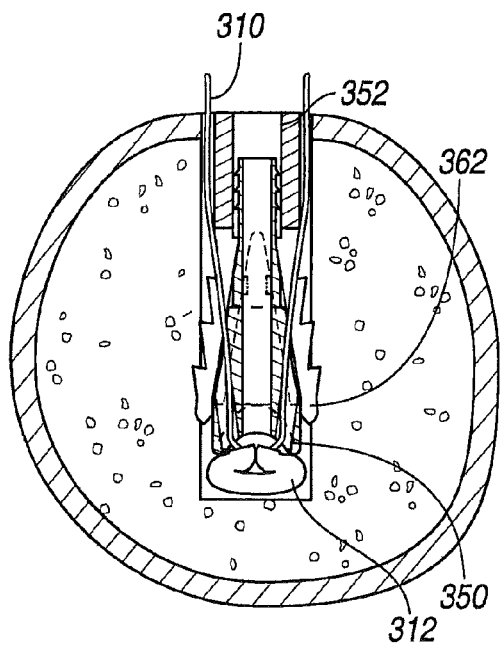

As best shown in FIGS. 26B and 26C, the first and second portions of the fastener 350, 352 are fed over an insertion tool 354. Disposed on the first portion 350 of the fastener 348 is a suture 310 having the flexible sleeve 312 threaded thereon. Threaded through an optional pair of apertures 311 within the first fastener portion 350 is a pair of ends of the suture 310. These ends are then threaded through a central bore or a slot defined in the second fastener portion 352.

After the insertion of the fastener 348 into a bore 302 defined within the bone 304, the second fastener portion 302 is coupled to the first fastener portion 305. This coupling optionally causes an expansion of the bone engaging flanges 362. Tension can be applied to the ends of the suture 310 to cause the compression of the flexible member 312. This collapsing of the flexible member can then lock the suture 310 to the first and/or second portions of the fastener 350, 352.

The foregoing discussion discloses and describes merely exemplary arrangements. One skilled in the art will readily recognize from such discussion, and from the accompanying drawings and claims, that various changes, modifications and variations can be made therein without departing from the spirit and scope of the present teachings as defined in the following claims. For example, multiple fixation members can be inserted in bone and can be coupled to suture anchors as described. The suture anchors can be coupled to the anchors before or after the anchors are coupled to the bone.

What is claimed is:

1. A method for securing a strand to at least one fixation member for a surgical procedure, the at least one fixation member having a central body axis and a tissue engaging flange, the strand having first and second ends through a flexible sleeve having a first cross-section such that the first and second ends of the strand are outside the flexible sleeve, the method comprising:

passing the sleeve through a bore formed through the fixation member along the central body axis and transversely through the fixation member into an exterior channel of the fixation member in a first direction and in a first configuration such that the sleeve is completely outside the fixation member;

tensioning the strand;

moving the sleeve in a second direction different than the first direction; and changing the sleeve to a second configuration that cannot reenter into the bore from the exterior channel to secure the sleeve to the fixation member without tying the strand on the fixation member.

2. The method according to claim 1, wherein the flange is a helical flange.

3. The method according to claim 1, wherein the flange is generally perpendicular to the central body axis.

4. The method according to claim 1, wherein the fastener comprises a plurality of tissue engaging flanges.

5. The method according to claim 4, wherein the plurality of tissue engaging flanges are one of perpendicular to the central body axis and helically disposed about the central body axis.

6. The method of claim 1, wherein the sleeve has first and second ends and the first and second ends of the strand exit the sleeve from corresponding first and second openings of the sleeve.

7. The method of claim 6, wherein moving the sleeve in a second direction different than the first direction presses first and second ends of the sleeve against the fixation member.

8. The method of claim 1, further comprising:

forming a hole in tissue; and inserting the fixation member in the hole.

9. The method according to claim 1 wherein moving the sleeve in a second direction causes the sleeve to press against adjacent tissue, wherein the sleeve pressing against the tissue contributes to the fixation of the construct in the tissue.

10. A method for securing a strand to a bone with at least one fixation member for a surgical procedure comprising:

providing an elongated flexible strand having first and second ends passing through at least a portion of a longitudinal bore of a flexible sleeve such that the first and second ends of the flexible strand are outside the flexible sleeve;

folding the sleeve into a first U-shaped configuration;

pushing the sleeve completely through an aperture of the fixation member in a first direction in the first U-shaped configuration; and tensioning the strand to change the sleeve to a second configuration that cannot pass through the aperture of the fixation member by pulling the sleeve in the second direction.

11. A method for securing a strand to a bone with at least one fixation member for a surgical procedure comprising:

deforming a flexible sleeve into a first configuration, wherein the flexible sleeve has an inner bore and an elongated flexible strand having first and second ends and passing through at least a portion of the inner bore of the flexible sleeve such that the first and second ends of the flexible strand are outside the flexible sleeve;

pushing the sleeve through the bore of the fixation member in a first direction in the first configuration and into an exterior channel of the fixation member such that the sleeve is completely outside the fixation member; and tensioning the strand to change the sleeve to a second configuration that cannot reenter from the exterior channel into the bore of the fixation member by pulling the sleeve in the second direction.

12. The method of claim 11, wherein the exterior channel is defined on a tissue engaging flange of the fixation member.

13. The method of claim 11, wherein the exterior channel is defined on an exterior surface of the fixation member.

* * * * *